(12) United States Patent
Thomson et al.

(10) Patent No.: US 8,629,399 B2
(45) Date of Patent: Jan. 14, 2014

(54) METHODS AND APPARATUSES FOR MEASURING BIOLOGICAL PROCESSES USING MID-INFRARED SPECTROSCOPY

(75) Inventors: Alasdair Thomson, Warrenville, IL (US); Muibat Gbadomosi, Houston, TX (US); Rebecca Nicholson, Warrenville, IL (US); Helen Mason, Naperville, IL (US)

(73) Assignee: BP Corporation North America Inc., Houston, TX (US)

( * ) Notice: Subject to any disclaimer, the term of this patent is extended or adjusted under 35 U.S.C. 154(b) by 624 days.

(21) Appl. No.: 12/564,224

(22) Filed: Sep. 22, 2009

(65) Prior Publication Data

US 2011/0070602 A1    Mar. 24, 2011

(51) Int. Cl.
*G01J 5/02* (2006.01)

(52) U.S. Cl.
USPC .................................................. 250/339.09

(58) Field of Classification Search
USPC ............... 250/338.5, 339.01, 339.02, 339.06, 250/339.07, 339.08, 339.09, 339.11, 339.12
See application file for complete search history.

(56) References Cited

U.S. PATENT DOCUMENTS

| | | | |
|---|---|---|---|
| 4,130,481 A | 12/1978 | Chase et al. | 210/6 |
| 5,262,961 A | 11/1993 | Farone | 364/500 |
| 5,717,209 A | 2/1998 | Bigman et al. | 250/339 |
| 6,395,538 B1 * | 5/2002 | Naughton et al. | 435/288.7 |
| 6,630,672 B1 | 10/2003 | Brotherton et al. | 250/339.07 |
| 2002/0155541 A1 | 10/2002 | Naughton et al. | 435/69.1 |
| 2005/0208473 A1 | 9/2005 | Krichevsky et al. | 435/4 |
| 2005/0214889 A1 | 9/2005 | Kang et al. | 435/23 |

FOREIGN PATENT DOCUMENTS

| | | |
|---|---|---|
| JP | 63274840 | 11/1988 |
| JP | 5273124 | 10/1993 |
| WO | WO 95/11485 | 4/1995 |
| WO | WO 01/06233 | 1/2001 |
| WO | WO 02/082061 | 10/2002 |
| WO | WO 2009/121416 | 10/2009 |
| WO | WO 2009/121423 | 10/2009 |

OTHER PUBLICATIONS

Fayolle et al., On-line monitoring of fermentation processes by a new remote dispensive middle-infrared spectrometer, Elsevier, Food Control 11, (2000) pp. 291-296.
Kansiz et al., Mid-infrared spectroscopy coupled to sequential injection analysis for the on-line monitoring of the acetone-butanol fermentation process, Analytica Chimica Acta 438, (2001) pp. 175-186.
Pollard et al., Real-time analyte monitoring of a fungal fermentation, at pilot scale, using in situ mid-infrared spectroscopy, Bioprocess and Biosystems Engineering 24, (2001) pp. 13-24.

(Continued)

*Primary Examiner* — Mark R Gaworecki
(74) *Attorney, Agent, or Firm* — John P. Poliak

(57) ABSTRACT

This invention relates to methods and apparatuses for measuring biological processes using mid-infrared spectroscopy. The method includes the step of directing a mid-infrared signal into a sample of a biological process during a biologically active phase, and the step of detecting a sample spectrum from the mid-infrared signal to form a sample spectrum. The method includes the step of generating a reference spectrum through a reference media, and the step of combining the sample spectrum and the reference spectrum to form an adjusted sample spectrum.

14 Claims, 16 Drawing Sheets

(56) References Cited

OTHER PUBLICATIONS

Schenk et al., A simple method to monitor and control methanol feeding of *Pichia pastoris* fermentations using mid-IR spectroscopy, Journal of Biotechnology 128, (2007) 344-353.

V. Beilon et al.—"Fermentation control using ATR and an FT-IR spectrometer", Elsevier Sequoia S.A., Lausanne, CH, vol. 12 No. 1, (1993) pp. 57-64.

S. Bureau et al.—"Application of ATR-FTIR for a rapid and simultaneous determination of sugars and organic acids in apricot fruit", Food Chemistry, Elsevier Ltd, vol. 115 No. 3, 2009, pp. 1133-1140, www.elseiver.com/local/foodchem.

M. Pons—"Special analysis and fingerprinting for biomedia characterization", Journal of Biotechnology, Elsevier Science Publishers, Amsterdam, NL, vol. 113, No. 1-3, 2004, pp. 211-230.

P. Roychoudhury et al.—"The potential of mid infrared spectroscopy (MIRS) for real time bioprocess monitoring", Analytica Chimica Acta, Elsevier, vol. 571, 2006, pp. 159-166, www.sciencedirect.com.

E. Veale et al.—"An On-line approach to monitor ethanol fermentation using FTIR Spectroscopy", Biotechnolovy Progress, American Chemical Society and American Institute of Chemical Engineers, vol. 23, 200, pp. 294-500.

H. Yu et al.—"A feasibility study on on-line determination of rice wine composition by Vis-NIR spectroscopy and least-squares support vector machines", vol. 113, 2009, pp. 291-296.

\* cited by examiner

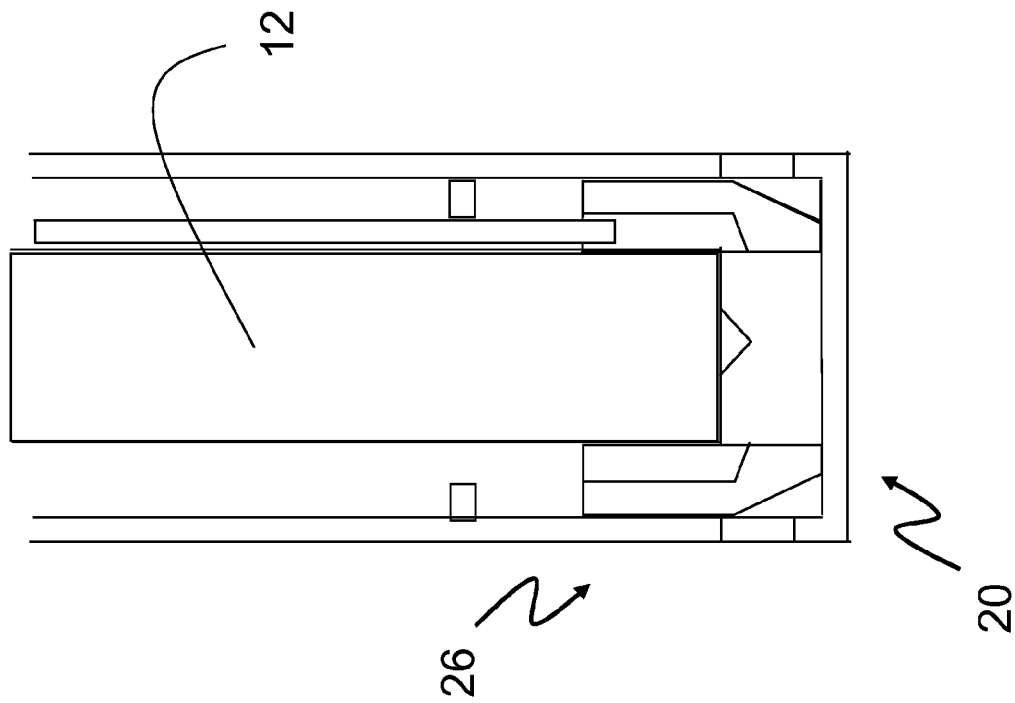
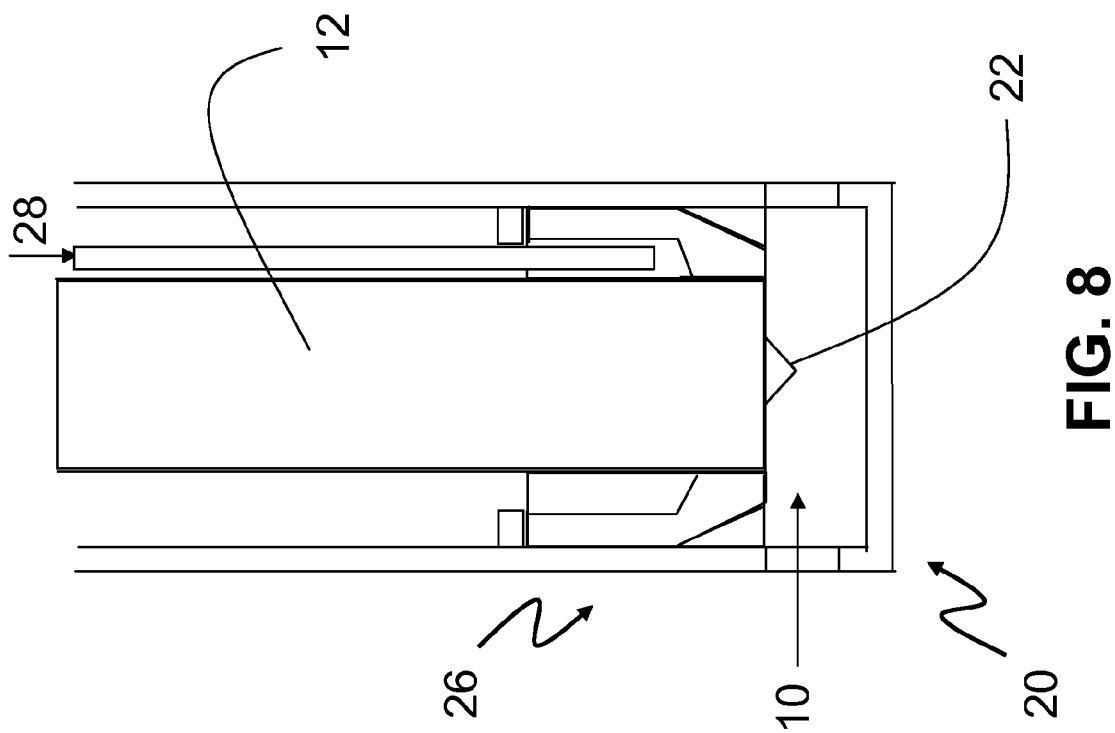

METHODS AND APPARATUSES FOR MEASURING BIOLOGICAL PROCESSES USING MID-INFRARED SPECTROSCOPY

BACKGROUND

1. Technical Field

This invention relates methods and apparatuses for measuring biological processes using mid-infrared spectroscopy.

2. Discussion of Related Art

Analytical instruments and/or techniques seek to measure and/or monitor processes. Gas chromatography, mass spectrometry, high performance liquid chromatography, and thermal calorimetry, represent known devices and/or procedures used to measure processes. Recent environmental concerns and limited natural resources have driven development and use of materials derived from non-fossilized materials, such as materials produced through biological processes. However, even with the above technology in analytical instruments and techniques, there remains a need and a desire for additional methods and apparatuses for measuring biological processes, such as detecting reactants, products, and/or by-products of the biological process while reliably operating on-line in the biological process.

SUMMARY

This invention relates to methods and apparatuses for measuring biological processes using mid-infrared spectroscopy. The methods and apparatuses can detect reactants, products, and/or by-products of the biological process while reliably operating on-line in the biological process.

According to a first embodiment, this invention includes a method for measuring biological processes. The method includes the step of directing a mid-infrared signal into a sample of a biological process during a biologically active phase, and the step of detecting a sample spectrum from the mid-infrared signal to form a sample spectrum. The method includes the step of generating a reference spectrum through a reference media, and the step of combining the sample spectrum and the reference spectrum to form an adjusted sample spectrum.

According to a second embodiment, this invention relates to a second method of measuring biological processes. The second method includes the step of directing a mid-infrared signal into an initial sample of a biological process, and the step of detecting a sample spectrum from the mid-infrared signal to form an initial sample spectrum. The second method includes the step of generating an initial reference spectrum through a reference media. The second method includes the step of combining the initial sample spectrum and the initial reference spectrum to form an adjusted initial sample spectrum, and the step of directing the mid-infrared signal into one or more subsequent samples of the biological process. The second method includes the step of detecting a sample spectrum from the mid-infrared signal to form one or more subsequent sample spectra, and the step of generating one or more subsequent reference spectra through the reference media corresponding to each of the one or more subsequent sample spectra. The second method includes the step of combining the one or more subsequent sample spectra and the corresponding one or more subsequent reference spectra to form one or more adjusted subsequent sample spectra, and the step of subtracting the adjusted initial sample spectrum from each of the one or more adjusted subsequent sample spectra to form one or more difference spectra.

According to a third embodiment, this invention relates to an apparatus for measuring biological processes. The apparatus includes a mid-infrared spectrometer, and a probe optically connected with the spectrometer and adapted for fluid communication with at least a portion of a biological process. The apparatus includes a reference media optically connected with the spectrometer.

BRIEF DESCRIPTION OF THE DRAWING

The accompanying drawings, which are incorporated in and constitute a part of this specification, illustrate embodiments of the invention and, together with the description, serve to explain the features, advantages, and principles of the invention. In the drawings, FIG. 1 schematically shows a biological process, according to one embodiment;

FIG. 8 schematically shows a probe housing in an open position, according to one embodiment;

FIG. 9 schematically shows the probe housing of FIG. 8 in a closed position;

DETAILED DESCRIPTION

This invention relates to methods and apparatuses for measuring biological processes using mid-infrared spectroscopy. According to one embodiment, the invention may include measuring an absorbance spectrum of interstitial spaces of a spectrometer with an independent fiber optic reference loop to produce a background spectrum. The method may include measuring an absorbance spectrum of a biological process immediately following inoculation to produce an initial spectrum. The method may include subtracting the background spectrum from the initial spectrum to produce a reference spectrum. At a point later in time, the invention may include measuring an absorbance spectrum of the interstitial spaces of the spectrometer with the independent fiber optic reference loop to produce a second background spectrum. Also at the later point in time, the method may include measuring an absorbance spectrum of the biological process to produce a later spectrum. The method may include taking a ratio of the second background spectrum and the later spectrum to produce a process spectrum. The method may include subtracting the reference spectrum from the process spectrum to produce a product spectrum.

Without being bound by theory, the method can correct for features within the spectrum that may lessen accuracy and/or specificity of the spectrometer, such as water vapor, carbon dioxide, and/or the like. The method can enhance features that would otherwise be hidden by peaks of the background and/or contaminants.

According to one embodiment, the invention can be described at least in part by the following equations.

$$\text{Absorbance}(A) = -\log(I/I_0) = a \cdot b \cdot c$$

$$\begin{aligned} A &= -\log(Is/Is_0) \\ &= -\log(Is/Ir \cdot Ir/Is_0) \\ &= -\log(Is/Ir) - \log(Ir/Is_0) \\ &= -\log(Is/Ir) + \log(Is_0/Ir) \\ &= Asr - As_0r \end{aligned}$$

Where s=sample and r=reference loop.

Figure 1:
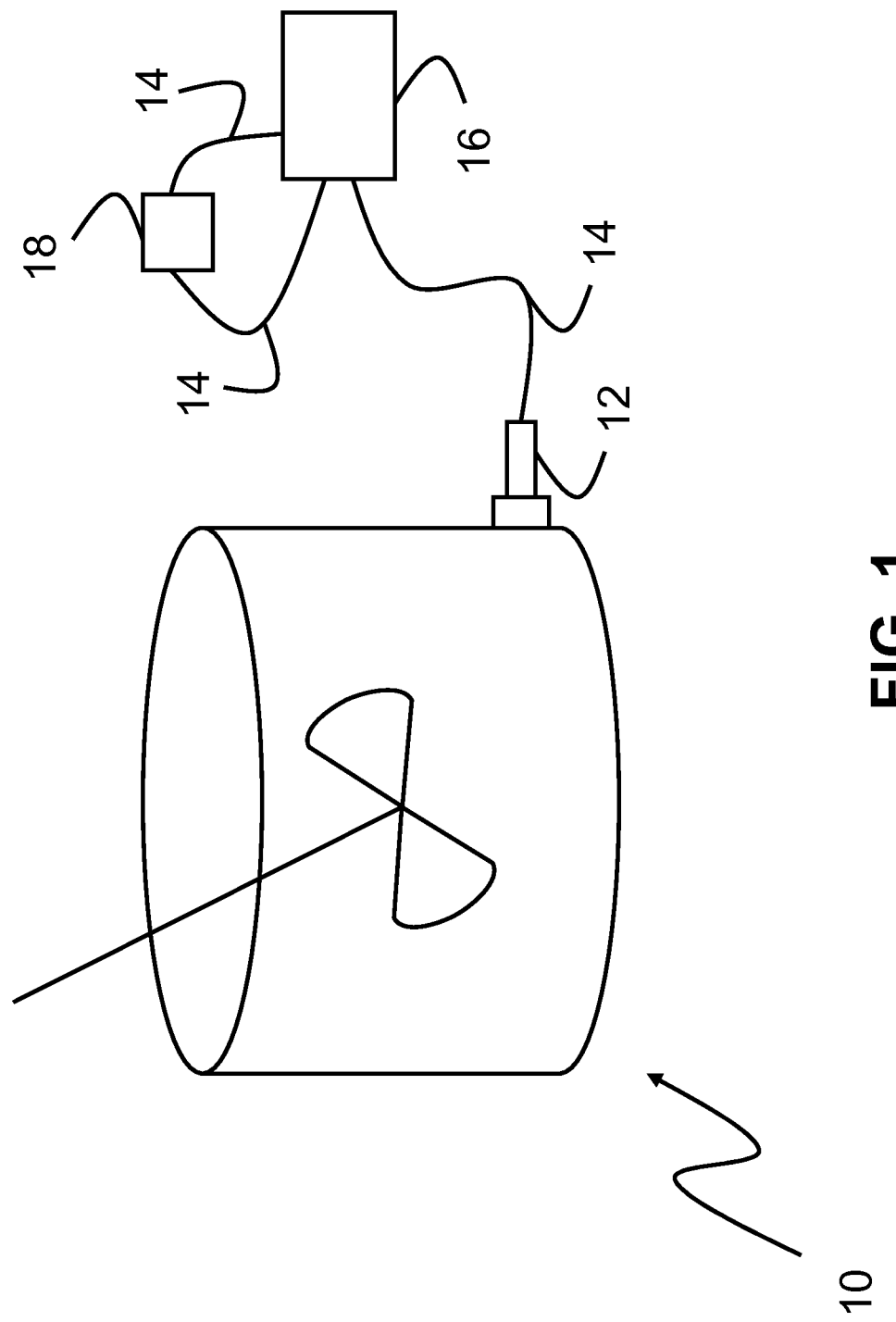

FIG. 1 schematically shows a biological process 10, according to one embodiment. The biological process 10 uses a reaction vessel. The biological process 10 can be measured with a mid-infrared probe 12 connected by fiber optic cables 14 to a spectrometer 16. The spectrometer 16 also connects with a reference media 18 by fiber optic cables 14.

Figure 2:
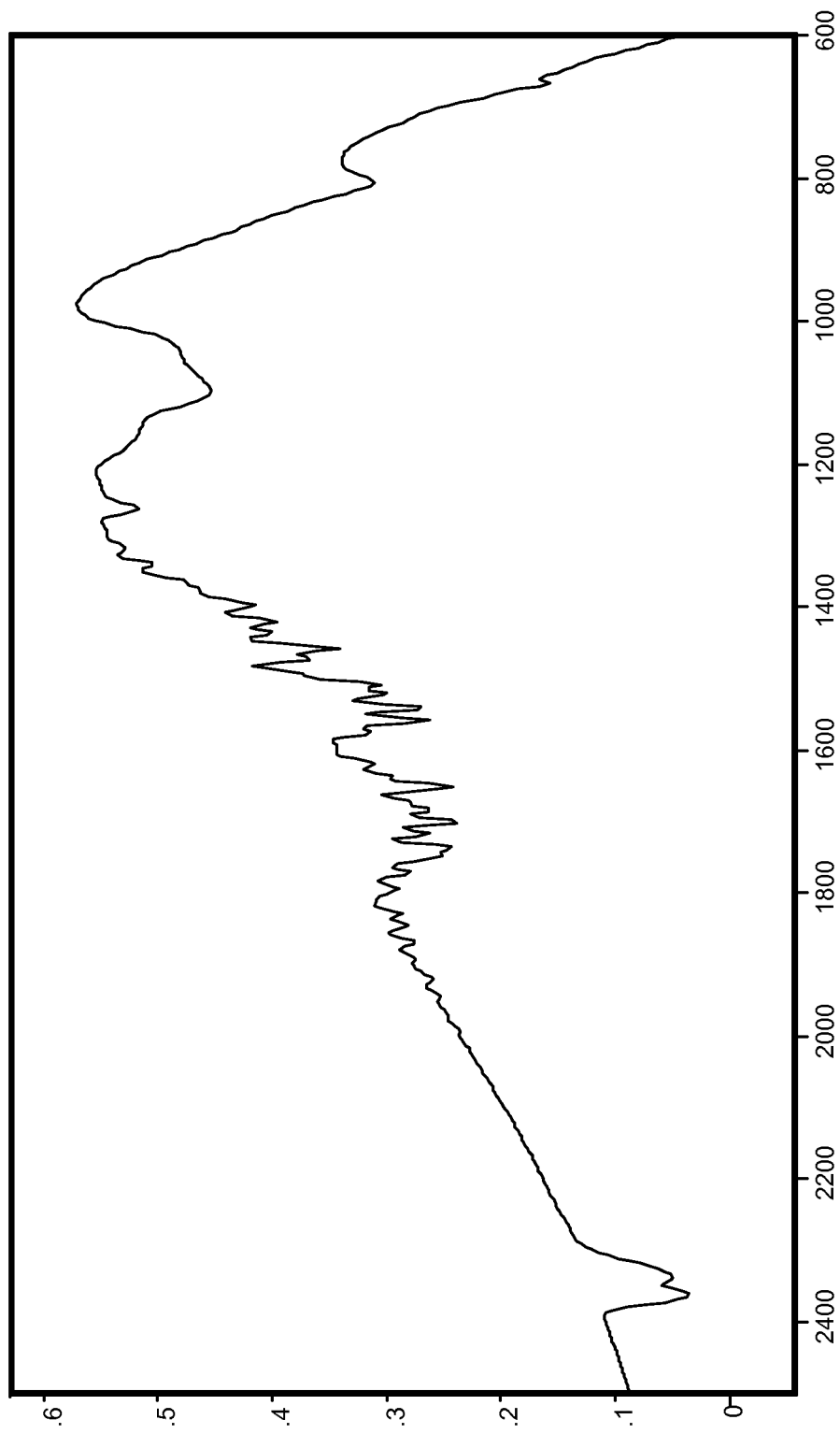
FIG. 2 shows an initial reference spectrum, according to one embodiment.

FIG. 2 shows an initial reference spectrum as a graph of wave numbers (centimeters$^{-1}$) on the x-axis and absorbance (absorbance units) on the y-axis. The initial reference spectrum includes water vapor features between about 800 centimeters$^{-1}$ and about 1,100 centimeters$^{-1}$. The initial reference spectrum includes carbon dioxide features between about 2,300 centimeters$^{-1}$ and about 2,400 centimeters$^{-1}$.

Figure 3:
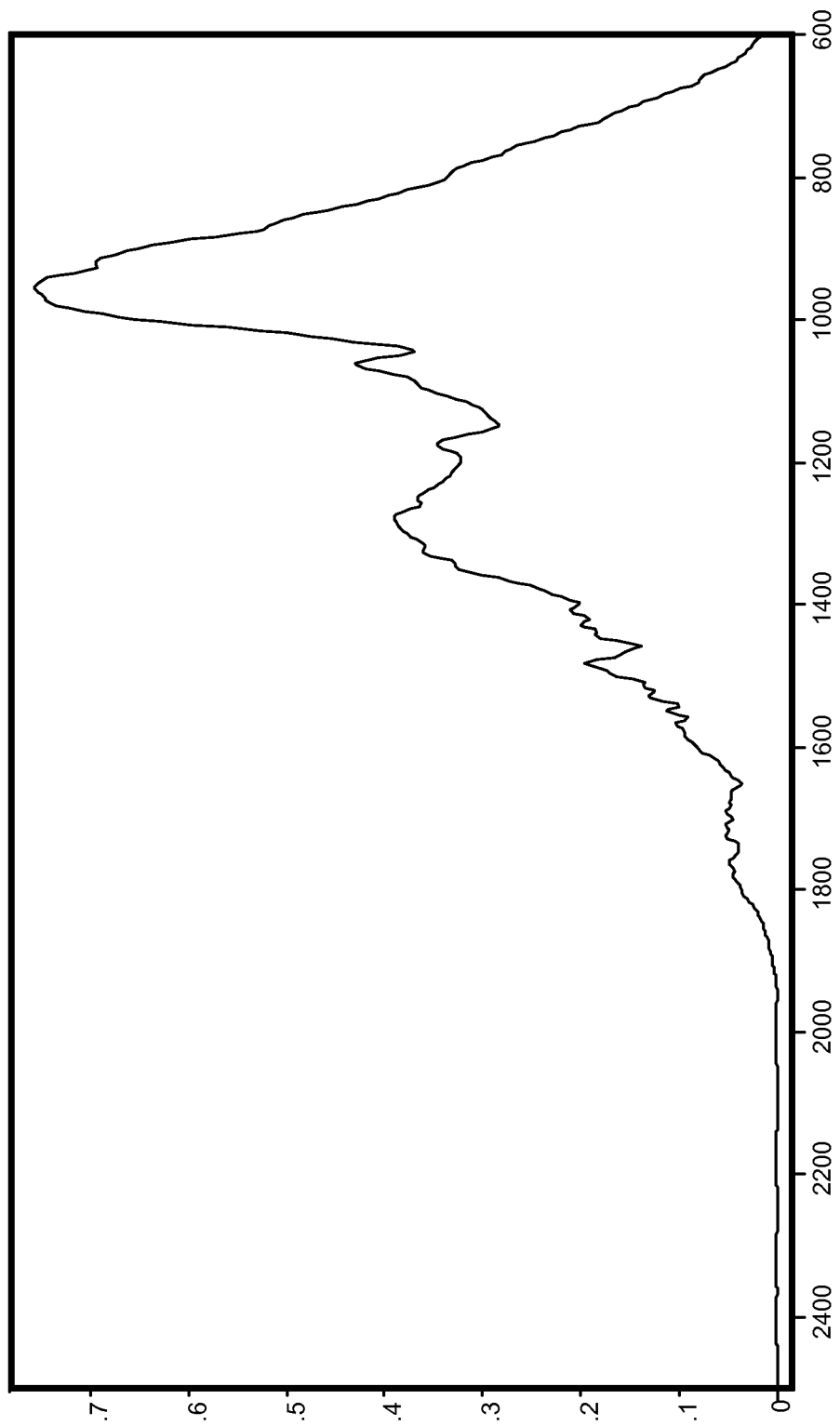
FIG. 3 shows an initial sample spectrum, according to one embodiment.

FIG. 3 shows an initial sample spectrum as a graph of wave numbers (centimeters$^{-1}$) on the x-axis and absorbance (absorbance units) on the y-axis.

Figure 4:
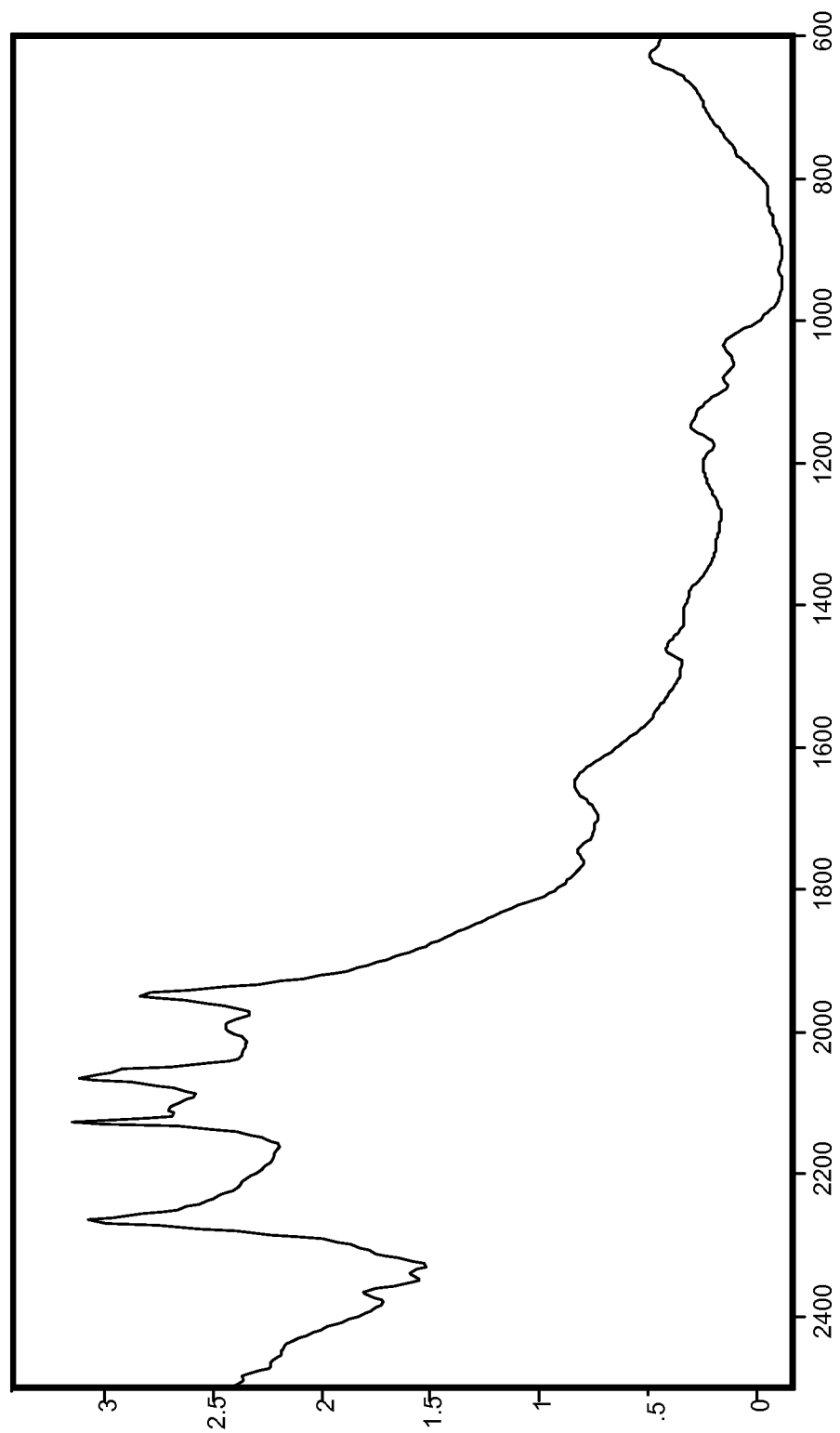
FIG. 4 shows an adjusted initial sample spectrum, according to one embodiment.

FIG. 4 shows an adjusted initial sample spectrum as a graph of wave numbers (centimeters$^{-1}$) on the x-axis and absorbance (absorbance units) on the y-axis. The adjusted initial sample spectrum of FIG. 4 was derived from combining the initial sample spectrum of FIG. 3 and the initial reference spectrum of FIG. 2.

Figure 5:
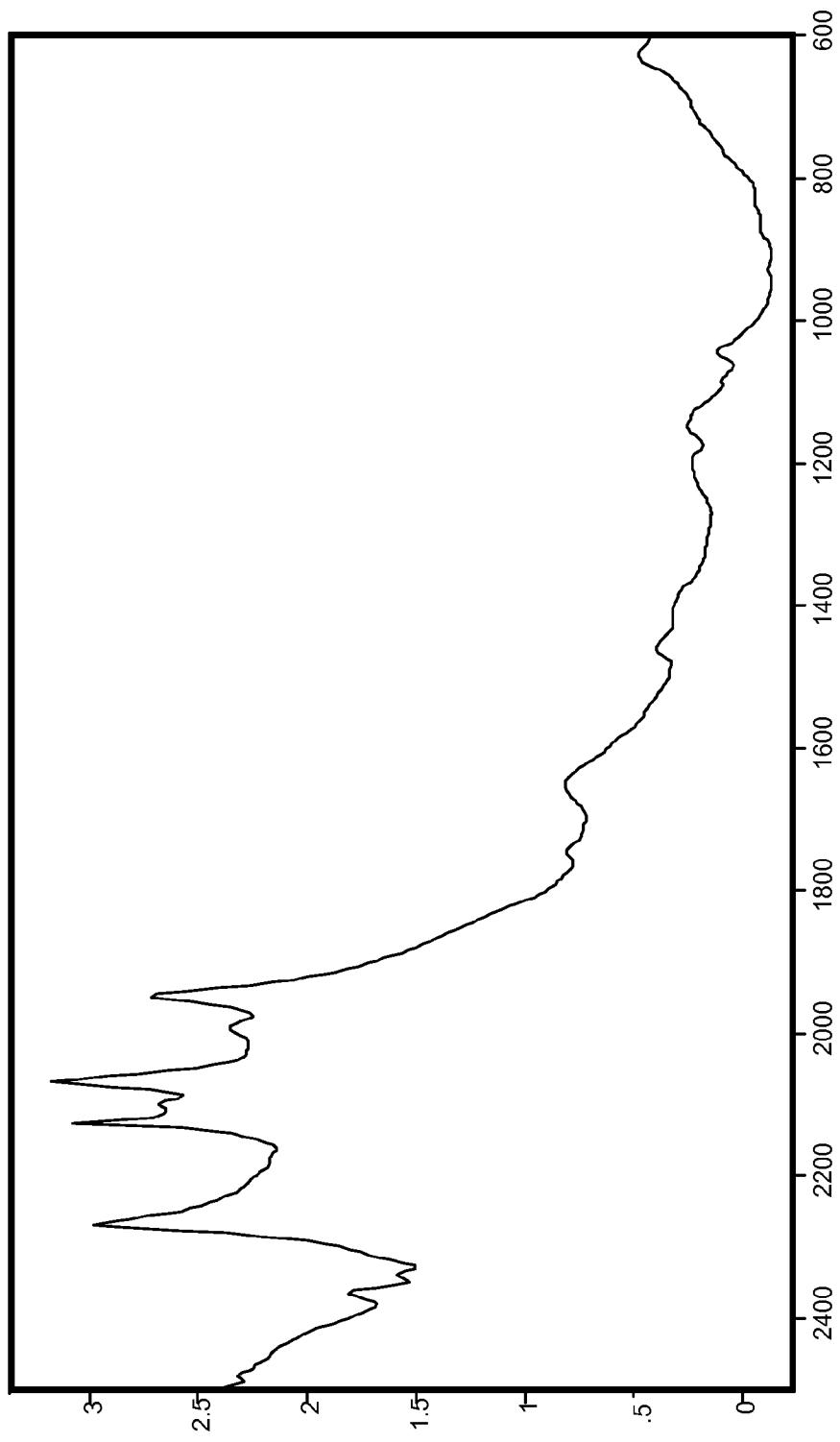
FIG. 5 shows an adjusted subsequent sample spectrum, according to one embodiment.

FIG. 5 shows an adjusted subsequent sample spectrum as a graph of wave numbers (centimeters$^{-1}$) on the x-axis and absorbance (absorbance units) on the y-axis. The adjusted subsequent sample spectrum of FIG. 5 was derived from combining a subsequent sample spectrum (not shown) and a subsequent reference spectrum (not shown).

Figure 6:
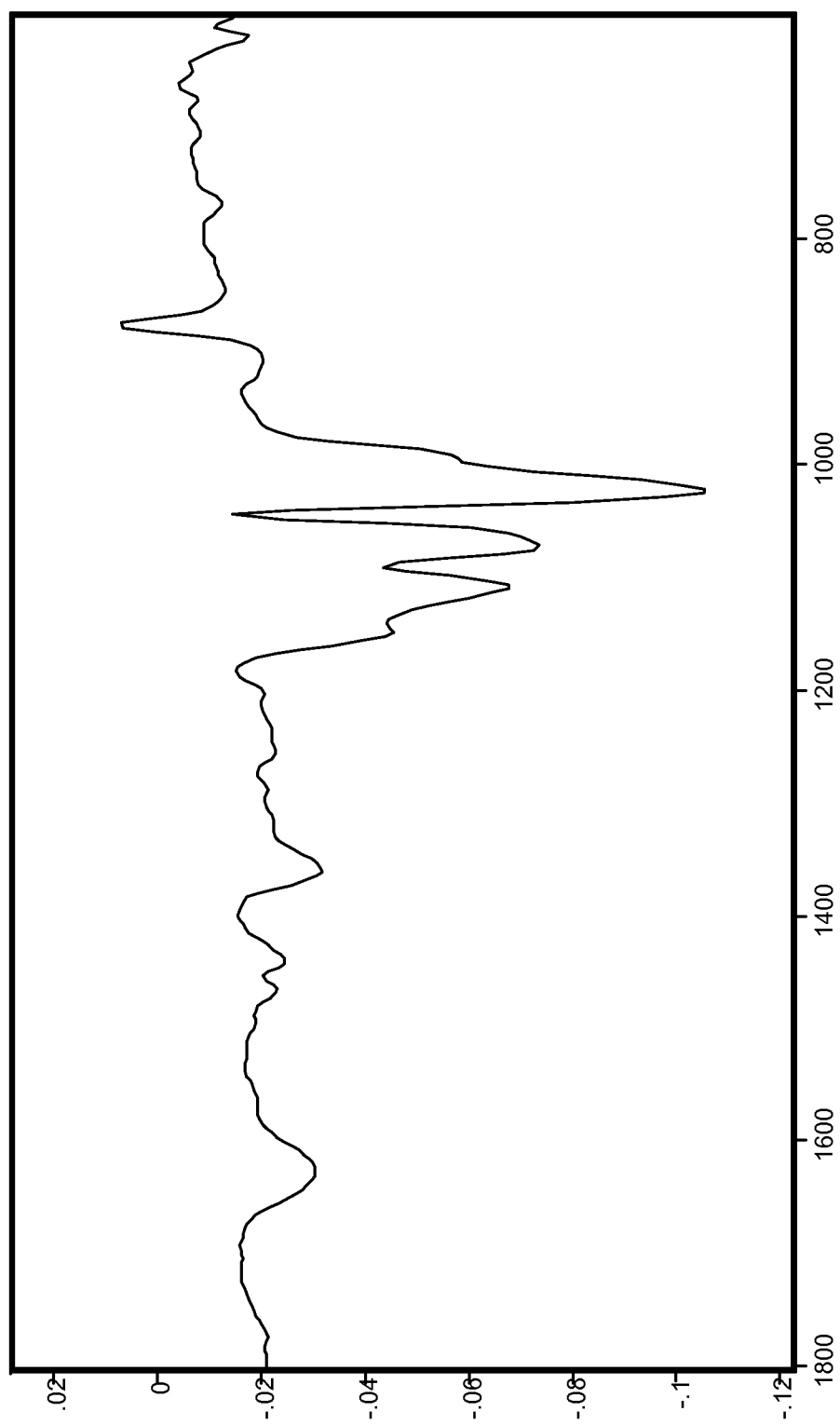
FIG. 6 shows a difference spectrum, according to one embodiment.

FIG. 6 shows a difference spectrum as a graph of wave numbers (centimeters$^{-1}$) on the x-axis and absorbance (absorbance units) on the y-axis. The difference spectrum of FIG. 6 was derived from subtracting the adjusted initial sample spectrum of FIG. 4 from the subsequent reference spectrum of FIG. 5. The difference spectrum shows the spectrum between 600 centimeters$^{-1}$ and 1,800 centimeters$^{-1}$. The difference spectrum can be suitable for chemometric model development.

Figure 7:
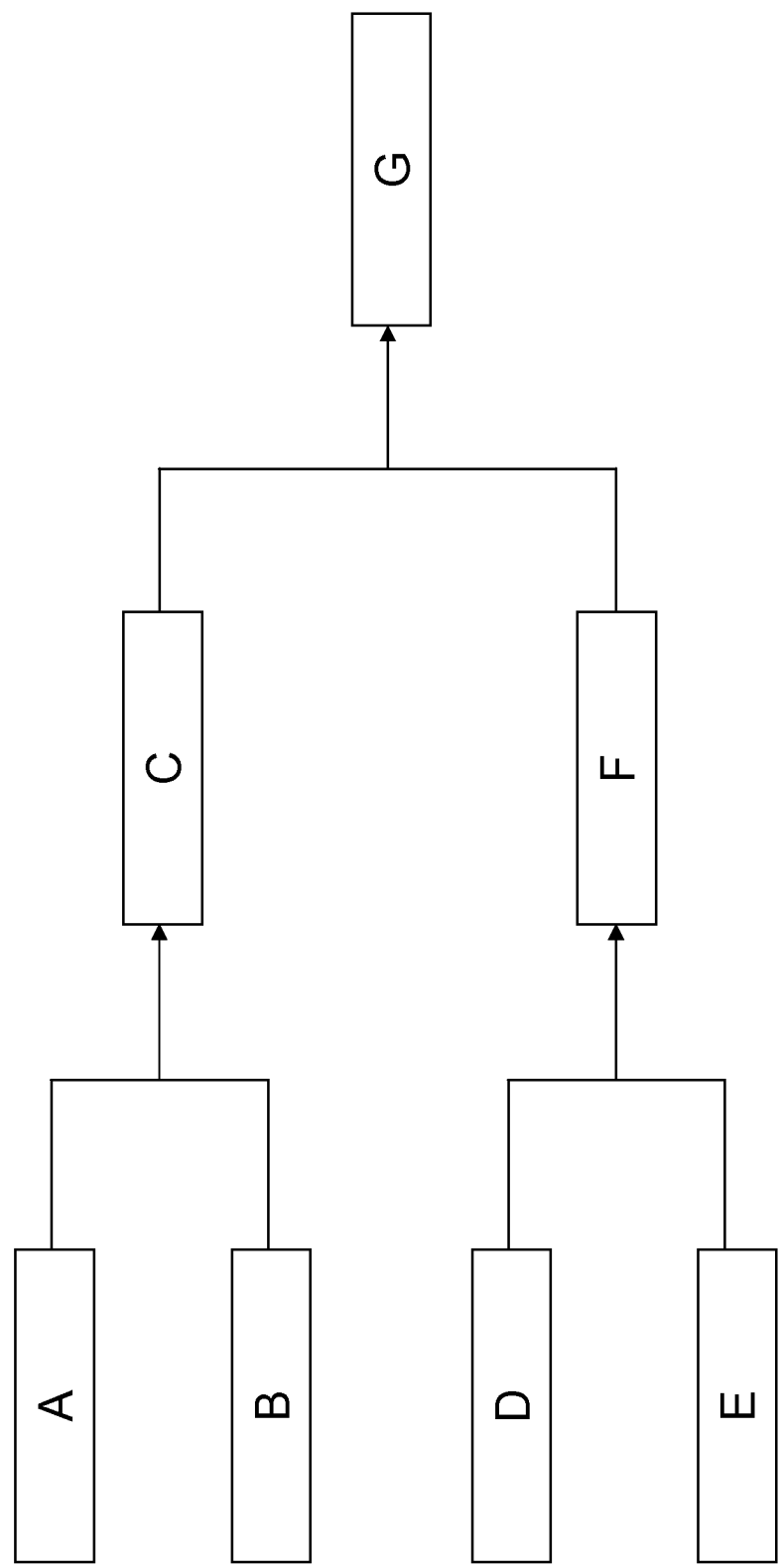
FIG. 7 schematically shows a method flow sheet, according to one embodiment.

FIG. 7 schematically shows a flow sheet of a method of measuring a biological process, according to one embodiment. Block A represents the step of generating an initial reference spectrum through a reference media. Block B represents the steps of directing a mid-infrared signal into an initial sample of a biological process, and detecting a sample spectrum from the mid-infrared signal to form an initial sample spectrum. Block C represents the step of combining the initial sample spectrum (Block B) and the initial reference spectrum (Block A) to form an adjusted initial sample spectrum (Block C).

Block D represents the step of generating one or more subsequent reference spectra through the reference media. Block E represents the steps of directing the mid-infrared signal into one or more subsequent samples of the biological process, and detecting a sample spectrum from the mid-infrared signal to form one or more subsequent sample spectra corresponding to each of the one or more subsequent reference spectra. Block F represents the step of combining the one or more subsequent sample spectra (Block E) and the corresponding one or more subsequent reference spectra (Block D) to form one or more adjusted subsequent sample spectra (Block F).

Block G represents the step of subtracting the adjusted initial sample spectrum (Block C) from each of the one or more adjusted subsequent sample spectra (Block F) to form one or more difference spectra (Block G).

FIG. 8 schematically shows a probe 12 and a probe housing 20 with an isolation device 26 in an open position to the biological process 10, according to one embodiment. The probe 12 has a probe surface 22 which contacts the biological process 10 and can be cleaned with a flush fluid 28. The probe housing 20 includes a retaining ring, a vent slot, a filling slot, a process slot, a seal ring, and optionally a chamfer. Desirably, the probe housing 20 includes an annular geometry movable and/or slidable between open, intermediate, and/or closed positions.

FIG. 9 schematically shows the probe 12 and the probe housing 20 of FIG. 8 with the isolation device 26 in a closed position to the biological process 10 (not shown), according to one embodiment.

Figure 10:
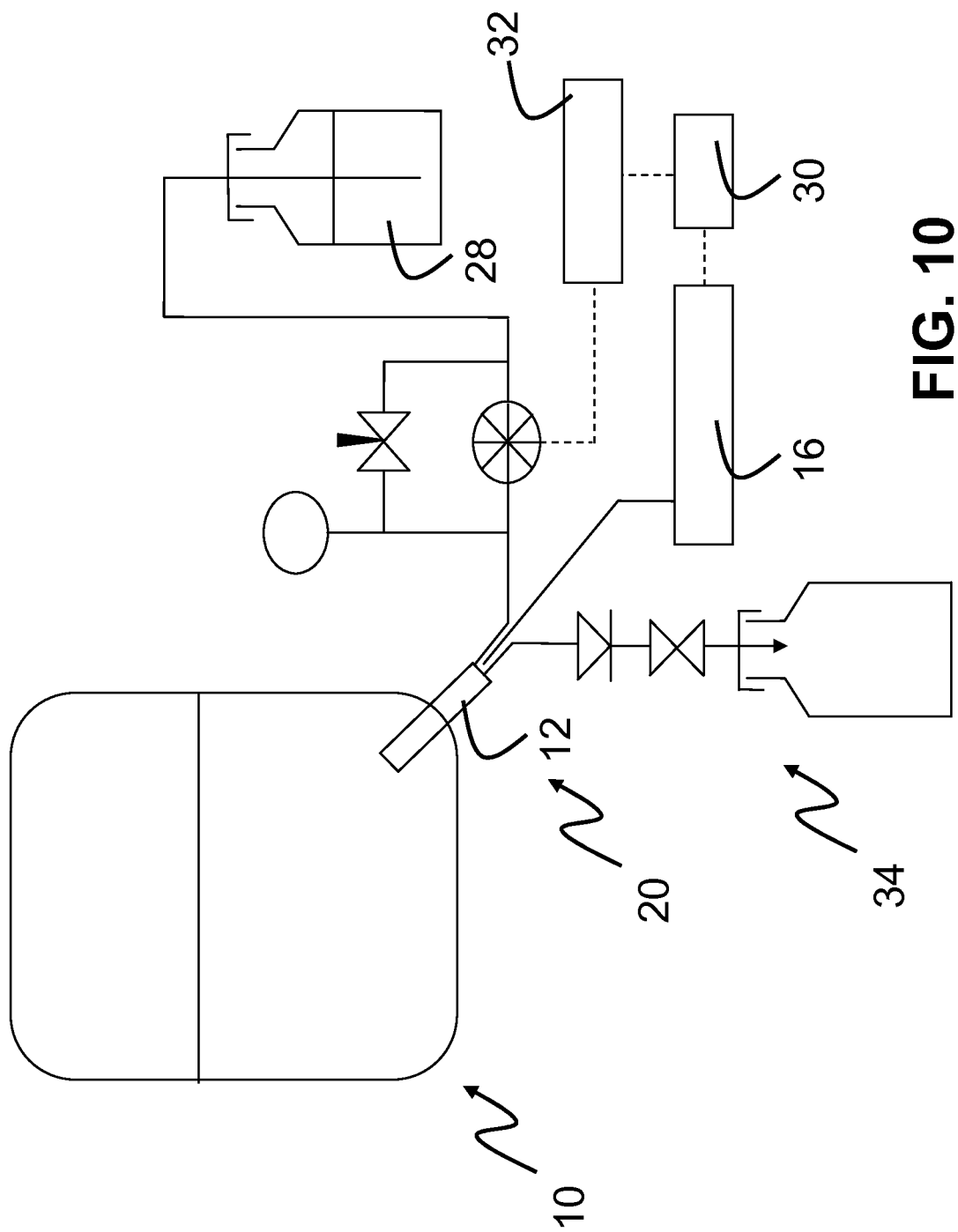
FIG. 10 schematically shows a biological process, according to one embodiment.

FIG. 10 schematically shows a biological process 10, according to one embodiment. A probe 12 inserts through a probe housing 20 and into the biological process 10. The probe 12 connects to a spectrometer 16. The probe housing 20 connects with a flush system 34 for a flush fluid 28. The flush system 34 includes connecting piping, tubing, valves, fittings, pumps, reservoirs, and/or the like. The flush system 34 has a controller 32 and connects to a computer 30 which also connects to the spectrometer 16.

According to one embodiment, the invention may include a method of measuring biological processes. The method may include the step of directing a mid-infrared signal into a sample of a biological process during a biologically active phase, and the step of detecting a sample spectrum from the mid-infrared signal to form a sample spectrum. The method may include the step of generating a reference spectrum through a reference media, and the step of combining the sample spectrum and the reference spectrum to form an adjusted sample spectrum.

Measuring broadly refers to ascertaining, detecting, scaling, gauging, and/or the like of an amount and/or a quantity, such as mole percent of a constituent. Constituents and/or components can be measured on any suitable basis, such as a molar basis, a mass basis, a volume basis, and/or the like.

Process broadly refers, to steps, actions and/or events, such as leading to a result and/or an outcome. Processes may be continuous, discrete, batch, semi-continuous, semi-batch, and/or the like.

Biological broadly refers to life systems, living processes and/or alive organisms, such as archaea, bacteria, and/or eukarya. According to one embodiment biological includes biologically derived compounds, such as enzymes, proteins, and/or the like. According to one embodiment biological excludes fossilized and/or ancient materials, such as those whose life ended at least about 1,000 years ago.

Biological processes may include any suitable living system and/or item derived from a living system and/or steps, such as fermentation, cell culturing, aerobic respiration, anaerobic respiration, catabolic reactions, anabolic reactions, biotransformation, saccharification, liquefaction, hydrolysis, depolymerization, polymerization, and/or the like.

Directing broadly refers to pointing, extending, projecting, shining, illuminating, and/or the like.

Signal broadly refers an object used to transmit and/or convey information, such as a detectable physical quantity and/or impulse. According to one embodiment, the signal comprises a steady beam of light with an appropriate frequency. In the alternative, the signal may include varying and/or pulsing with changes in wavelength, frequency, amplitude, phase, and/or the like.

Mid-infrared broadly refers to a portion of the electromagnetic spectrum with a wavelength longer than visible light but shorter than microwaves, such as a wave number of between about 4,000 centimeters$^{-1}$ to about 400 centimeters$^{-1}$, between about 3,000 centimeters$^{-1}$ and about 1,000 centimeters$^{-1}$, between about 1,500 centimeters$^{-1}$ and about 2,500 centimeters$^{-1}$, and/or the like. Mid-infrared light may have any suitable wavelength, such as between about 30 micrometers and about 2.5 micrometers, between about 25 micrometers and about 5 micrometers, and/or the like. Mid-infrared may be used to study fundamental vibrations and associated rotational-vibrational structures, such as symmetrical stretching, asymmetrical stretching, scissoring, rocking, wagging, twisting, and/or the like.

Into broadly refers to entry, introduction, insertion, inclusion, and/or the like.

Sample broadly refers to a representative part and/or a portion of a larger whole and/or group, such as having a quality and/or aspect of the whole. According to one embodiment, the sample can be taken from a portion of a contents of a biological reaction vessel. According to one embodiment, the sample can be taken by direct insertion into a biological reaction vessel. Samples can be withdrawn from a bulk phase, taken in situ, taken on-line, taken off-line, taken externally, and/or the like.

During broadly refers to through a duration or period.

Biologically active phase broadly refers to during a period of active biological processes, such as a cell metabolism, biotransformation, cell growth, and/or the like. According to one embodiment, the biologically active phase includes inactive and/or dormant stages. In the alternative and according to one embodiment, the biologically active phase may exclude inactive and/or dormant stages, such as just before and/or just after inoculation without significant cellular activity within the biological process. According to one embodiment, the biologically active phase includes lag phase, exponential phase, log phase, stationary phase, decline phase, death phase, and/or the like.

Detecting broadly refers to discovering, determining, measuring, an existence, a presence, a fact and/or the like.

Spectra broadly refer to ranges of frequencies and/or wavelengths, such as may include continuous ranges and/or discrete ranges. The spectra can show how much transmitted light to reveal how much energy has been absorbed at each wavelength.

Desirably, the sample spectrum with peaks and/or valleys corresponds to elements, compounds, molecules, constituents, and/or the like of the biological process. The sample spectrum can correspond and/or represent any suitable time and/or period during the biological process, such as during activation, during a first conversion period, during a second conversion period, during a third conversion period, during a fourth conversion period, during a concluding period and/or the like. Any suitable amount of available feedstock corresponding to the sample spectra can be converted, such as at least about 10 percent, at least about 20 percent, at least about 30 percent, at least about 40 at least about 50 percent, at least about 60 percent, at least about 70 percent, at least about 80 percent, at least about 90 percent, and/or the like, on a mass basis.

The sample spectrum can be taken at any suitable frequency, such as at least about 1 per second, at least about 1 per minute, at least about 1 per 5 minutes, at least about 1 per 10 minutes, at least about 4 per hour, at least about 1 per hour, at least about 1 per 4 hours, at least about 1 per 8 hours, at least about 2 per day, at least about 1 per day, at least 1 per 2 days, at least about 1 per 5 days, at least about 1 per week, at least about 1 per 2 weeks, and/or the like.

Generating broadly refers to making, collecting, originating, bringing into existence, and/or the like.

Reference broadly refers to something referred or consulted, such as a source of information.

Reference media broadly refers to any suitable substance, such as useful for improving a quality and/or content of a reading of the biological process. The reference media may include water, fermentation material, air, fiber optic cable, and/or the like. The reference media may include a closed sample of the media through which a mid-infrared signal can be directed. The fermentation material may be representative of any suitable point in the process, such as at a start point of a fermentation cycle, at a midpoint of a fermentation cycle, at an endpoint of a fermentation cycle, and/or the like. The reference media can supply an air background, a water background, a background corresponding to inside the spectrometer, and/or the like. Without being bound by theory, the fiber optic loop can allow removal of features that may change over time with changes of operation of the spectrometer (internal conditions). The fiber optic loop can include a single fiber optic cable connecting from a light source of the spectrometer to a detector. According to one embodiment, the fiber optic loop excludes other devices and/or media.

Without being bound by theory, variations of conditions within a spectrometer may create noise and/or a lack of clarity in the signal from the biological process. The use of a reference spectrum can remove and/or filter the noise in the sample spectrum. The noise can be created by changes in water vapor content (humidity), carbon dioxide content, and/or the like within the spectrometer. For example, when monitoring a fermentation system, sample spectra can be taken at a beginning of fermentation after inoculation with microorganisms. Even though the spectrometer may be hermetically sealed, a water vapor content of within the spectrometer may change during the biological process, such that subsequent samples may include noise from the change in water vapor as detected by the spectrometer. Use of the reference media can reduce and/or remove noise from the spectra.

Combining broadly refers to adding, subtracting, multiplying, dividing, taking logarithms, taking exponents, taking ratios, completing transforms (LaPlace, Fourier, and/or the like), taking derivatives, taking integrals, and/or any other suitable mathematical manipulation of the sample spectrum and the reference spectrum. According to one embodiment, the reference spectrum can be subtracted from the sample spectrum to form and/or make an adjusted sample spectrum.

Desirably, the methods and apparatuses of the invention can provide real time and/or on-line data or information for the biological process. The probe may interface with the process in situ or outside of the process, for example.

The mid-infrared signal can penetrate into the sample at any suitable depth, such as between about 1 micron and about 10 microns, between about 2 microns and about 8 microns, between about 3 microns and about 7 microns, between about 4 microns and about 6 microns, at least about 2 microns, at least about 3 microns, and/or the like. Passing the mid-infrared signal through the sample can form a transmitted signal and/or a reflected signal.

The reference spectrum, the sample spectrum, and/or the adjusted sample spectrum can include values corresponding to molecular stretching, molecular bending, and/or the like. The reference spectrum, the sample spectrum, and/or the adjusted sample spectrum can contain values corresponding to carbon single bonds (between about 900 centimeters$^{-1}$ to about 1,500 centimeters$^{-1}$), carbon double bonds (between about 1,500 centimeters$^{-1}$ to about 1,800 centimeters$^{-1}$), carbon triple bonds (between about 2,100 centimeters$^{-1}$ to about 2,300 centimeters$^{-1}$), carbon-oxygen bonds, carbon-nitrogen bonds, oxygen-hydrogen bonds (between about 3,300 centimeters$^{-1}$ and about 3,500 centimeters$^{-1}$), nitrogen-hydrogen bonds, and/or the like. Carbon double bonds may include carbon-carbon bonds, carbon-oxygen bonds, carbon-nitrogen bonds, and/or the like. Carbon triple bonds may include carbon-carbon bonds, carbon-nitrogen bonds, and/or the like.

The reference spectrum, the sample spectrum, and/or the adjusted sample spectrum can contain values corresponding to any suitable material, element, compound, and/or molecule, such as acetone, acetaldehyde, ethanol, butanol, pentanol, isoprenol, isoprene, butyraldehyde, acetic acid, lactic acid, pyruvic acid, glycerol, pentose, hexose, fatty alcohols, fatty acids, acylglycerides (including monoglycerides, diglycrides, triglycerides), carbon dioxide, carbon monoxide, and/or the like.

According to one embodiment, the biological process includes production and/or manufacture of renewable materials. Renewable materials broadly refer to substances and/or items that have been at least partially derived from a source and/or process capable of being replaced by natural ecological cycles and/or resources. Renewable materials may broadly include chemicals, chemical intermediates, solvents, monomers, oligomers, polymers, biofuels, biofuel intermediates, biogasoline, biogasoline blendstocks, biodiesel, green diesel, renewable diesel, biodiesel blend stocks, biodistillates, and/or the like. Desirably, but not necessarily, the renewable material may be derived from a living organism, such as plants, algae, bacteria, fungi, and/or the like.

Biofuel broadly refers to components or streams suitable for use as a fuel or a combustion source derived from renewable sources, such as those which may be sustainably produced and/or have reduced or no net carbon emissions to the atmosphere. According to one embodiment, renewable resources may exclude materials mined or drilled, such as from the underground. Desirably, renewable resources may include single cell organisms, multicellular organisms, plants, fungi, bacteria, algae, cultivated crops, non-cultivated crops, timber, and/or the like. Biofuels may be suitable for use as transportation fuels, such as for use in land vehicles, marine vehicles, aviation vehicles, and/or the like. Biofuels may be suitable for use in power generation, such as raising steam and/or making electricity.

Biogasoline broadly refers to components or streams suitable for direct use and/or blending into a gasoline pool and/or octane supply derived from renewable sources, such as methane, hydrogen, syngas (synthesis), methanol, ethanol, propanol, butanol, dimethyl ether, methyl tert-butyl ether, ethyl tert-butyl ether, hexanol, aliphatic compounds (straight, branched, and/or cyclic), heptane, isooctane, cyclopentane, aromatic compounds, ethyl benzene, and/or the like. Butanol broadly refers to products and derivatives of 1-butanol, 2-butanol, iso-butanol, other isomers, and/or the like. Biogasoline may be used in spark ignition engines, such as automobile gasoline internal combustion engines. According to one embodiment, the biogasoline and/or biogasoline blends meet or comply with industrially accepted fuel standards.

Biodiesel broadly refers to components or streams suitable for direct use and/or blending into a diesel pool and/or cetane supply derived from renewable sources, such as fatty acid esters, triglycerides, lipids, fatty alcohols, alkanes, naphthas, distillate range materials, paraffinic materials, aromatic materials, aliphatic compounds (straight, branched, and/or cyclic), and/or the like. Biodiesel may be used in compression engines, such as automotive diesel internal combustion engines. In the alternative, the biodiesel may also be used in gas turbines, heaters, boilers, and/or the like. According to one embodiment, the biodiesel and/or biodiesel blends meet or comply with industrially accepted fuel standards.

Biodistillate broadly refers to components or streams suitable for direct use and/or blending into aviation fuels (jet), lubricant base stocks, kerosene fuels, and/or the like derived from renewable sources, and having a boiling point range of between about 100 degrees Celsius and about 700 degrees Celsius, between about 150 degrees Celsius and about 350 degrees Celsius, and/or the like.

According to one embodiment, the biological process comprises biomass fermentation to an alcohol. Biomass broadly refers to plant and/or animal materials and/or substances derived at least in part from living substances, such as lignocellulosic sources.

Lignoellulosic broadly refers to containing cellulose, hemicellulose, lignin, and/or the like, such as plant material. Lignocellulosic material may include any suitable material, such as sugar cane, sugar cane bagasse, energy cane, energy cane bagasse, rice, rice straw, corn, corn stover, wheat, wheat straw, maize, maize stover, sorghum, sorghum stover, sweet sorghum, sweet sorghum stover, cotton, cotton remnant, sugar beet, sugar beet pulp, soybean, rapeseed, jatropha, switchgrass, miscanthus, other grasses, timber, softwood, hardwood, wood bark, wood waste, sawdust, paper, paper waste, agricultural waste, manure, dung, sewage, municipal solid waste, any other suitable biomass material, and/or the like.

According to one embodiment, the step of directing a mid-infrared signal utilizes attenuated total reflectance having at least about 1 reflection and/or bounce of the mid-infrared signal off an internal surface in fluid communication with the at least a portion of the biological process. The number of reflections and/or bounces can be any suitable number, such as at least about 1, at least about 2, at least about 3, at least about 3.4, at least about 4, at least about 6, at least about 8, at least about 10, at least about 12, and/or the like.

The step of detecting a sample spectrum from the mid-infrared signal to form a sample spectrum may include detecting the mid-infrared signal reflected and/or transmitted from the sample of the biological process.

According to one embodiment, the method may also include the step of directing the mid-infrared signal into an initial sample of the biological process before the biologically active phase and the step of detecting a sample spectrum from the mid-infrared signal to form an initial sample spectrum before the biologically active phase. The method may include the step of generating an initial reference spectrum through the reference media before the biologically active phase, and the step of combining the initial sample spectrum and the initial reference spectrum to form an adjusted initial sample spectrum. The method may also include the step of subtracting and/or combining the adjusted initial sample spectrum from and/or with the adjusted sample spectrum to form a difference spectrum.

Initial broadly refers to relating to a beginning, such as incipient.

Before the biologically active phase broadly refers to a period without significant cellular activity, such as before inoculation or addition of the microorganisms to the biological process and/or soon thereafter, such as less than about 10 minutes, less than about 5 minutes, less than about 2 minutes, and/or the like. Before the biologically active phase may include a period of time following charging of the feedstock and liquid into the biological process vessel, such as sugar and water.

The subtracting and/or combining to form the difference spectrum may include any of the suitable mathematical manipulations and/or techniques described above with respect to forming the adjusted sample spectrum.

The difference spectrum shows a change in transmittance of the biological process from the beginning of the biological process to a subsequent period, such as to show a change in concentration of a material. The difference spectra can be useful for compounds and/or products formed during the biological process. Additional difference spectra corresponding to other time periods (before and/or after) are within the scope of this invention.

Optionally and/or alternately, for compounds being consumed by the biological process (feedstocks) the sample adjusted spectra or a portion thereof can be subtracted from the initial adjusted sample spectra. According to one embodiment, an absolute value of the difference spectrum can show a change in concentration from a compound based on the difference spectra. Desirably, the spectra can show an increase (typically products and/or by-products) in concentration and/or a decrease in concentration (typically reactants).

According to one embodiment, the method may further include the step of displaying one or more spectra on a display screen (monitor), printing one or more spectra on a printing substrate (paper); recording one or more spectra on a recording media (magnetic disk, flash memory, laser readable disk), and/or the like. The process may include any suitable tangible result and/or outcome.

Raw and/or bare spectral data can be converted into useful data by application of chemometric models. Chemometrics broadly refer to a science of relating measurements made on a chemical process to a state of a system, such as by application and/or use of mathematical and/or statistical methods or techniques. Chemometrics can be used to build a relationship (calibration model) between known concentrations of components present in a biological process, such as fermentation broth (state of the system) and the mid-infrared spectra collected from the biological process (measurements made on the process). Chemometric models can be based on variation and/or correlation in the data.

The spectral data can be converted to a new set of data based on different contributions to observed variation within the original data set. The new data set can consist of orthogonal components made from linear combinations of the absorbances at each wave number, such as factors of the principle components, for example. A number of factors for each component in the model can then be limited so that the factors that maximize the information on the process are included in the predictive model.

According to one embodiment, the invention may include a method of measuring biological processes. The method may include the step of directing a mid-infrared signal into an initial sample of a biological process, and the step of detecting a sample spectrum from the mid-infrared signal to form an initial sample spectrum. The method may include the step of generating an initial reference spectrum through a reference media, and the step of combining the initial sample spectrum and the initial reference spectrum to form an adjusted initial sample spectrum. The method may include the step of directing the mid-infrared signal into one or more subsequent samples of the biological process, and the step of detecting a sample spectrum from the mid-infrared signal to form one or more subsequent sample spectra. The method may include the step of generating one or more subsequent reference spectra through the reference media corresponding to each of the one or more subsequent sample spectra, and the step of combining the one or more subsequent sample spectra and the corresponding one or more subsequent reference spectra to form one or more adjusted subsequent sample spectra. The method may include the step of subtracting the adjusted initial sample spectrum from each of the one or more adjusted subsequent sample spectra to form one or more difference spectra.

According to one embodiment, the steps of the any of the methods disclosed herein can be executed in the number, frequency, and order explicitly listed herein. In the alternative, the steps of the method may be reordered, repeated, omitted, and/or the like.

Subsequent broadly refers to following in time, order, place, and/or the like, such as later. Subsequent may include any suitable period and/or frequency, such as about 1 per minute, about 1 per 10 minutes, about 1 per hour, about 1 per 2 hours, about 1 per 4 hours, about 1 per 8 hours, about 1 per day, and/or the like.

According to one embodiment, the mid-infrared signal can include wave numbers of between about 4,000 centimeters$^{-1}$ to about 400 centimeters$^{-1}$, and the reference media can include fiber optic cable. The biological process can include batch biomass fermentation to an alcohol, such as pentose and/or hexose to ethanol.

The method may also include the step of combining the one or more difference spectra to generate one or more time dependent spectra, such as to measure a change in concentration of a constituent during periods of time in a batch process.

According to one embodiment, the invention may include an apparatus for measuring biological processes. The apparatus and/or device may include a mid-infrared spectrometer, and a probe optically connected with the spectrometer. The probe may be adapted for fluid communication with at least a portion of a biological process. The apparatus can include a reference media optically connected with the spectrometer, such as on a separate channel and/or light source.

Any and/or all of the attributes and/or characteristics described above with respect to any portion of the method embodiments may be applied to the apparatus embodiments of the invention.

Spectrometer broadly refers to an instrument used for measuring wavelengths of light and/or spectra, such as an analytical instrument with an emission source and a detector to measure dispersion and/or transmittance from the emission source. Desirably, the spectrometer may be sealed and/or isolated from a surrounding environment. According to one embodiment, the spectrometer can generate a signal with wave numbers of between about 4,000 centimeters$^{-1}$ to about 400 centimeters$^{-1}$. The spectrometer may include cooling and/or chilling to a suitable temperature, such as with a suitable heat sink. Operating temperatures may include less than about 100 degrees Celsius, about ambient conditions, less than about 0 degrees Celsius, less than about −100 degrees Celsius, less than about −190 degrees Celsius, and/or the like.

Probe broadly refers to a testing device suitable for insertion into at least a portion of a process. The probe may include a crystal, such as diamond, sapphire, and/or the like. Desirably, but not necessarily, the probe may use attenuated total reflectance.

Optically connected may include any suitable conduit and/or cable, such as fiber optic cable, mirrored tubes, a visible path (line of sight), and/or the like. According to one embodiment, the apparatus excludes the use of a light pipe.

Fluid communication broadly refers to contacting at least a fluid and/or a liquid portion of a process, such as by direct insertion, a tubing connection, a piping connection, and/or the like.

As discussed above with respect to the method, the reference media of the apparatus may include water, air, fermentation material, fiber optic cable, and/or the like.

Also as discussed above with respect to the method, the probe can have at least 1 reflection of a mid-infrared signal off an internal surface in fluid communication with the at least a portion of the biological process.

The apparatus may include any other suitable equipment connected to the spectrometer, such as a computer. The computer may include any suitable components, such as a processor, a storage device, a display device, a printing device, a software program, and/or the like.

According to one embodiment, the apparatus may include a probe housing adapted with a flush mechanism to flow and/or pass a flush fluid across and/or over at least a portion of a probe surface. Without being bound by theory, solids and/or other materials in the biological process may foul and/or stick to a surface of the probe to reduce signal quality. The probe housing may be fabricated and/or constructed of any suitable material, such as carbon steel, stainless steel, nickel alloys, other alloys, polypropylene, polyethylene, polyvinyl chloride, fluoropolymers, engineered resins, other polymers, composite materials, and/or the like.

The flush fluid may include any suitable material, such as water, fermentation broth, ethanol, methanol, propanol, sugar solution, acetic acid, air, nitrogen, argon, carbon dioxide, other solvents, other diluents, and/or the like. The flush fluid may utilize a motive force device, such as a centrifugal pump, a positive displacement pump, and/or the like. The flush fluid may utilize one or more storage vessels, such as a reservoir, a tank, a bottle, a filter, and/or the like. The flush fluid and/or cleaning solution may use a gear pump to provide both forward flow and/or reverse flow.

Desirably, but not necessarily, the probe housing may provide movable isolation of the probe from the biological process, such as to provide a washing mode and/or operation. The probe housing may provide for in situ sterilization of wetted probe parts. An outer probe housing can be cleaned by steaming or other suitable procedures.

According to one embodiment, the probe housing may include an isolation device movable between an first position to expose at least a portion of the probe surface to the biological process and a second position to expose at least at least a portion of the probe surface to the flush fluid, such as with a generally annular concentric configuration. The isolation device may include a fluoropolymer probe seal moved between open and closed positions by hydraulic pressure, such as by electric switching of a gear pump in forward and/or reverse.

The probe can be flushed at any suitable frequency, such as about 1 per hour, about 1 per day, about 1 per 2 days, about 1 per week, and/or the like.

EXAMPLES

Example 1

Standards of ethanol (99.8 volume percent), D (+) glucose, sugar (Saccharose), malt extract, and brewer's yeast were the ingredients used to demonstrate capabilities and sensitivities of mid-infrared (MIR) techniques for biological processes.

Figure 11:
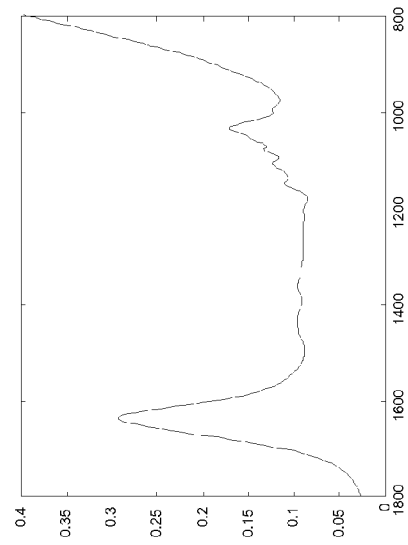
FIG. 11 shows a sugar spectrum, according to one embodiment.
Figure 12:
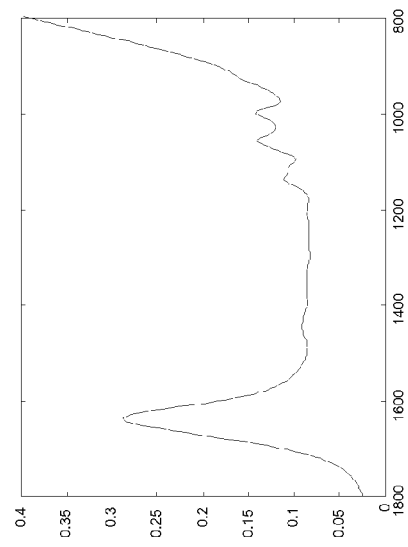
FIG. 12 shows a glucose spectrum, according to one embodiment.
Figure 13:
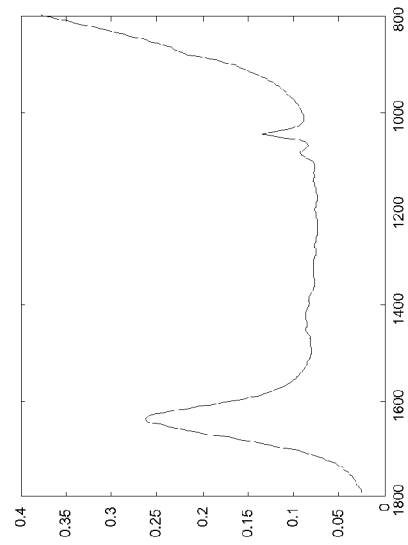
FIG. 13 shows a malt extract spectrum, according to one embodiment.
Figure 14:
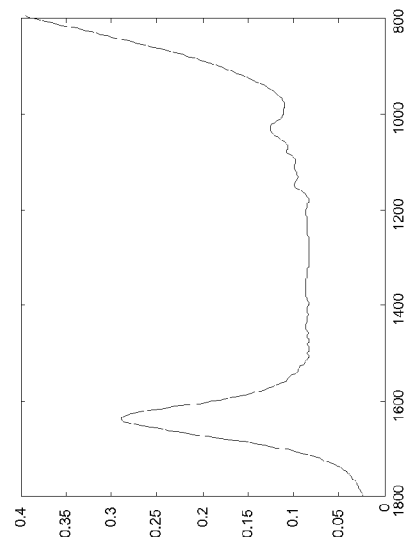
FIG. 14 shows an ethanol spectrum, according to one embodiment.

FIG. 11 shows a spectrum for the sugar standard with wave numbers (centimeters$^{-1}$) on the x-axis and absorbance (absorbance units) on the y-axis, according to one embodiment. FIG. 12 shows a spectrum for the glucose standard with wave numbers (centimeters$^{-1}$) on the x-axis and absorbance (absorbance units) on the y-axis, according to one embodiment. FIG. 13 shows a spectrum for the malt extract standard with wave numbers (centimeters$^{-1}$) on the x-axis and absorbance (absorbance units) on the y-axis, according to one embodiment. FIG. 14 shows a spectrum for the ethanol standard with wave numbers (centimeters$^{-1}$) on the x-axis and absorbance (absorbance units) on the y-axis, according to one embodiment.

A fermentation process was carried out by dissolving 80 grams of malt extract with 500 milliliters of boiling water in a sterilized beaker. 120 grams of sugar (glucose) was added to the beaker to form an aqueous solution. The aqueous solution was then transferred into a reaction vessel with continuous stirring and temperature control throughout the process. An additional 500 milliliters of water was added to the aqueous solution. 0.5 grams of yeast was dissolved in warm water for about 15 minutes before addition to the aqueous solution.

Spectroscopic data was acquired using a Bruker IFS166 FT-IR spectrometer from Bruker Optics Inc. in Billerica, Mass., U.S.A. The MIR spectra of the fermentation process were recorded hourly at 35 degrees Celsius with a dual bounce diamond attenuated total reflectance (ATR) probe from Fibre Photonics Ltd. in West Lothian, Scotland or Bruker Optics Inc. The ATR probe was connected to the spectrometer by polycrystalline infrared (PIR) fiber optic cables. The probe had a range of between 2,500 centimeters$^{-1}$ and 600 centimeters$^{-1}$ at an 8 centimeter$^{-1}$ resolution and accumulated 128 scans per spectrum. An initial background spectrum was taken at the start of each experiment. The spectrometer was equipped with a KBr (potassium bromide) beam-splitter and a Cryotiger cooler from Brooks Automation, Inc. Chelmsford, Mass. U.S.A. The cooler was coupled with a detector. The Cryotiger cooler was a low temperature refrigerator system which avoided a need for a separate liquid nitrogen cooling system.

The ATR probe was then inserted into the reaction vessel for recording spectra during a 75 hour glucose fermentation.

Figure 15:
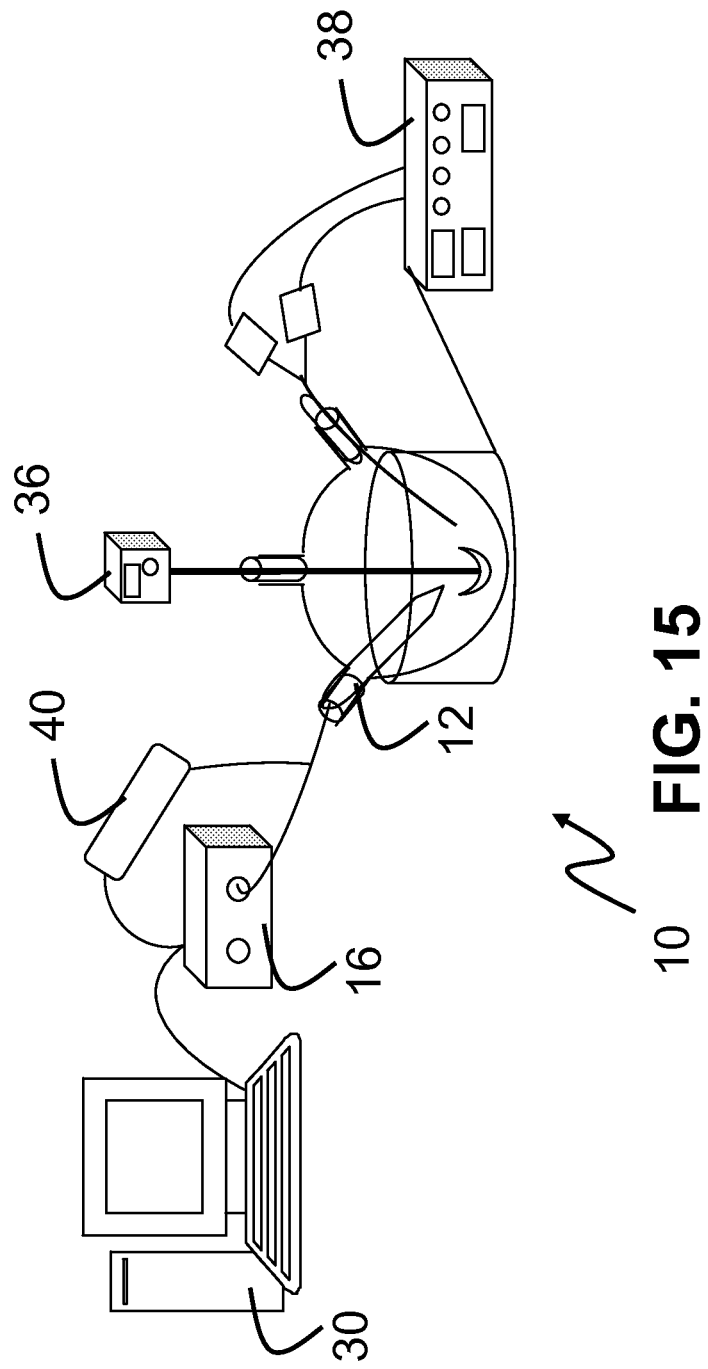
FIG. 15 shows an experimental set up, according to one embodiment.

FIG. 15 shows the experimental set up used in Example 1. The experimental set up includes a biological process 10 in a reaction vessel. A probe 12 inserts into the biological process 10 and connects to a spectrometer 16 and a detector 40 with a computer 30. The experimental set up includes a stirrer 36 and a temperature control device 38.

Figure 16:
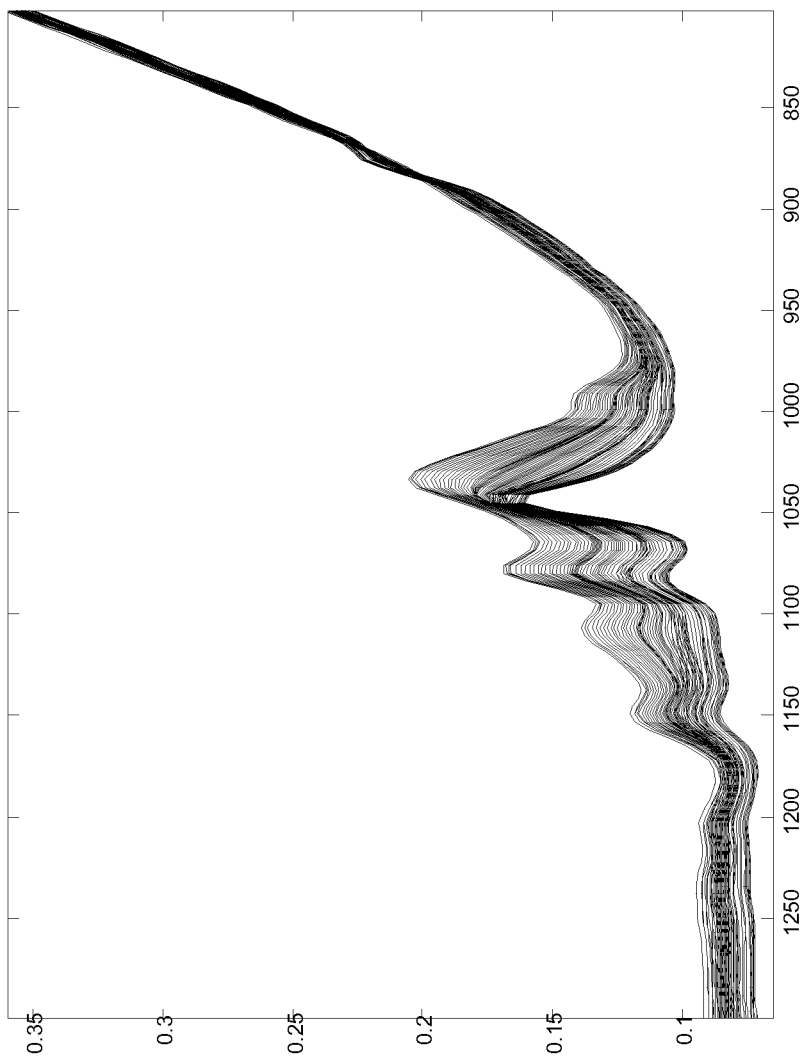
FIG. 16 shows fermentation spectra, according to one embodiment.

FIG. 16 shows spectra from the fermentation with wave numbers (centimeters$^{-1}$) on the x-axis and absorbance (absorbance units) on the y-axis. As time increased peaks corresponding to ethanol increased. Overlapping peaks can make univariate calibration difficult, so multivariate partial least squares techniques were applied. Chemometrics were used to analyze the spectra by using principal component analysis. Plots of the principal component analysis showed a downward trend consistent with consumption of the glucose and malt extract. The plot also showed no significant changes after about 55 hours which indicates fermentation yeast activity had ceased.

A partial least squares model was developed using 20 calibration standards with mixtures of glucose, malt extract, and ethanol based on first derivative pre-processing and second derivative pre-processing. The results of the correlations showed measured versus predicted values for $R^2$, coefficient of determination, of between 0.998 and 0.905.

The results of Example 1 showed that mid-infrared spectroscopy together with multivariate chemometric calibration can provide on-line monitoring of a fermentation process. The first and second derivative spectra along with the primary component analysis scores and loading plots gave explanatory information about the biotransformation of glucose to ethanol. The partial least squares model provided good estimates for the three components or analytes (glucose, malt extract, and ethanol), showing that the concentrations of the bio-process components can be predicted with accuracy for process monitoring.

The Cyrotiger detector facilitated continuous spectral acquisition without the need for a detector with liquid nitrogen cooling. The diamond ATR probe did not foul during the fermentation experiments.

Example 2

Four wheat flour fermentations were carried out on a 10 liter scale and monitored using mid-infrared spectroscopy. Several samples were collected from fermentation reactors for analysis. Chemometric models for glucose, glycerol, and ethanol were developed. Sterilization in place was also tested.

A Techfors-S stainless steel bioreactor with auxiliary equipment was used from INFORS HT, Bottmingen, Switzerland. An ATR probe was located in a spare bottom port of the reactor. Samples were collected from a sampling point on the bottom of the reactor.

Four fermentations were carried out over 4 weeks. Fermentation broths were prepared by treating a mixture of flour and water with liquefaction enzyme at 83 degrees Celsius followed by saccharification enzyme at 60 degrees Celsius. The broth was transferred aseptically into a fermentation vessel before inoculation with rehydrated yeast and 10 milliliters of 15 volume percent antifoam solution.

Run A used plain white flour at a temperature of 24 degrees Celsius, a yeast inoculation rate of 1.74 grams per liter of medium, and an agitation rate of 350 revolutions per minute. Run B used plain white flour at a temperature of 24 degrees Celsius, a yeast inoculation rate of 1.74 grams per liter of medium, and an agitation rate of 350 revolutions per minute. Run C used plain white flour at a temperature of 27 degrees Celsius, a yeast inoculation rate of 1.74 grams per liter of medium, and an agitation rate of 350 revolutions per minute. Run D used plain white flour at a temperature of 27 degrees Celsius, a yeast inoculation rate of 3.01 grams per liter of medium, and an agitation rate of 500 revolutions per minute.

The fermentation system was monitored with a 2 bounce ATR probe as used in Example 1. Sample acquisition included a reference spectrum from an independent fiber optic reference loop, measurement of the sample spectrum during the fermentation, and taking a ratio of the reference spectrum to the sample spectrum to form an adjusted sample spectrum for each period during fermentation. The samples were repeated every 5 minutes for a total of about 2,000 raw spectra per each of the four fermentations. The raw spectra were produced by subtracting an initial adjusted sample spectrum (just after inoculation) from the adjusted sample spectra to remove features that do not change overtime.

Fermentation broth samples were removed from the fermentation vessel about every 2 hours during a working week for about 20 samples per fermentation. Chemometric models were developed using portions of some of the samples by addition of known amounts of glucose, glycerol, and/or ethanol to form adjusted samples. A secondary demonstration probe was used to generate spectra for the adjusted samples. The adjusted samples were centrifuged and filtered before using high performance liquid chromatography (HPLC) on the resulting supernatant.

HPLC analysis had some issues of needle contamination, refractive index limitations, and co-elution of other sugars. HPLC issues may artificially increase error between the HPLC data and the mid-infrared data.

A calibration sample set included 59 samples from directly in the reactor and 61 samples from the adjusted samples. An additional 24 samples were retained for a validation set.

Figure 17:
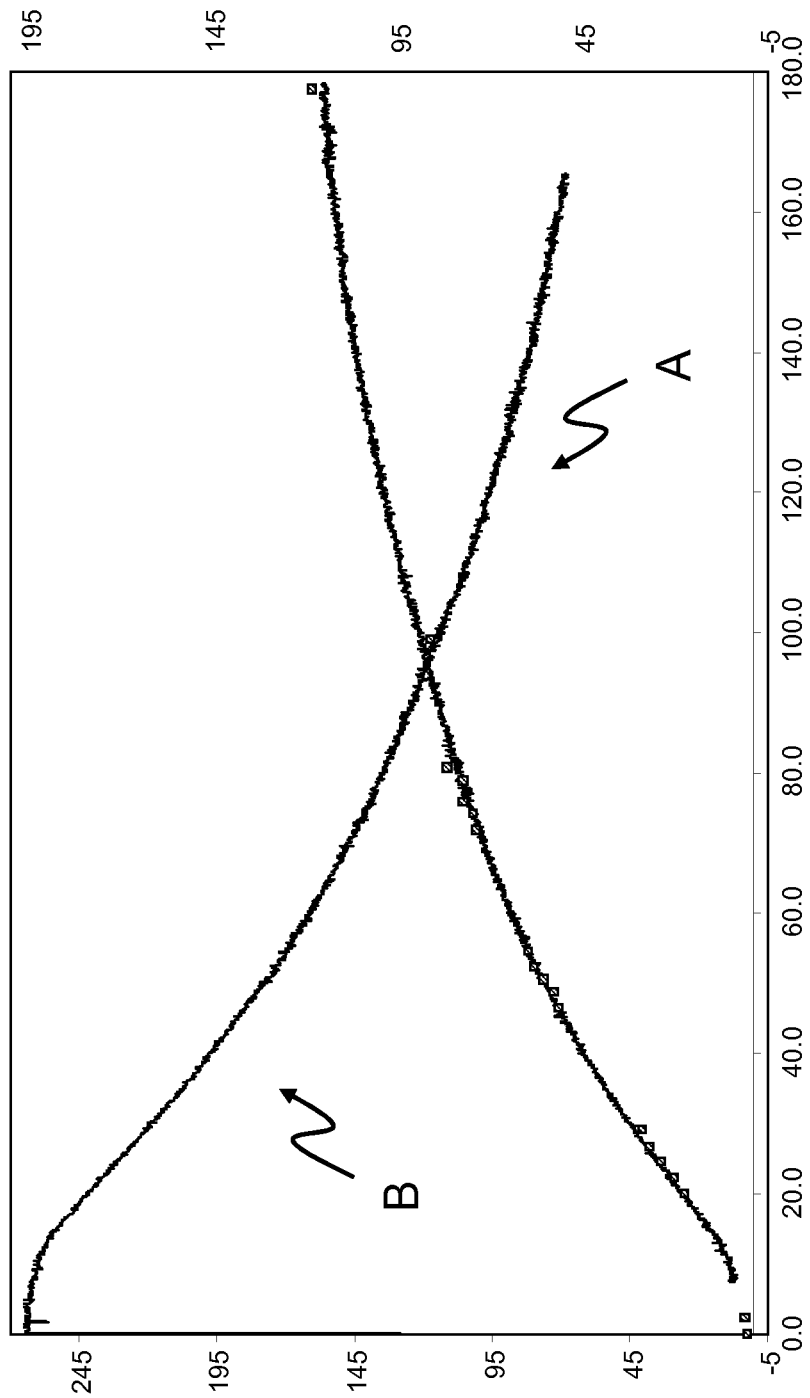
FIG. 17 shows time dependent spectra, according to one embodiment.
Figure 18:
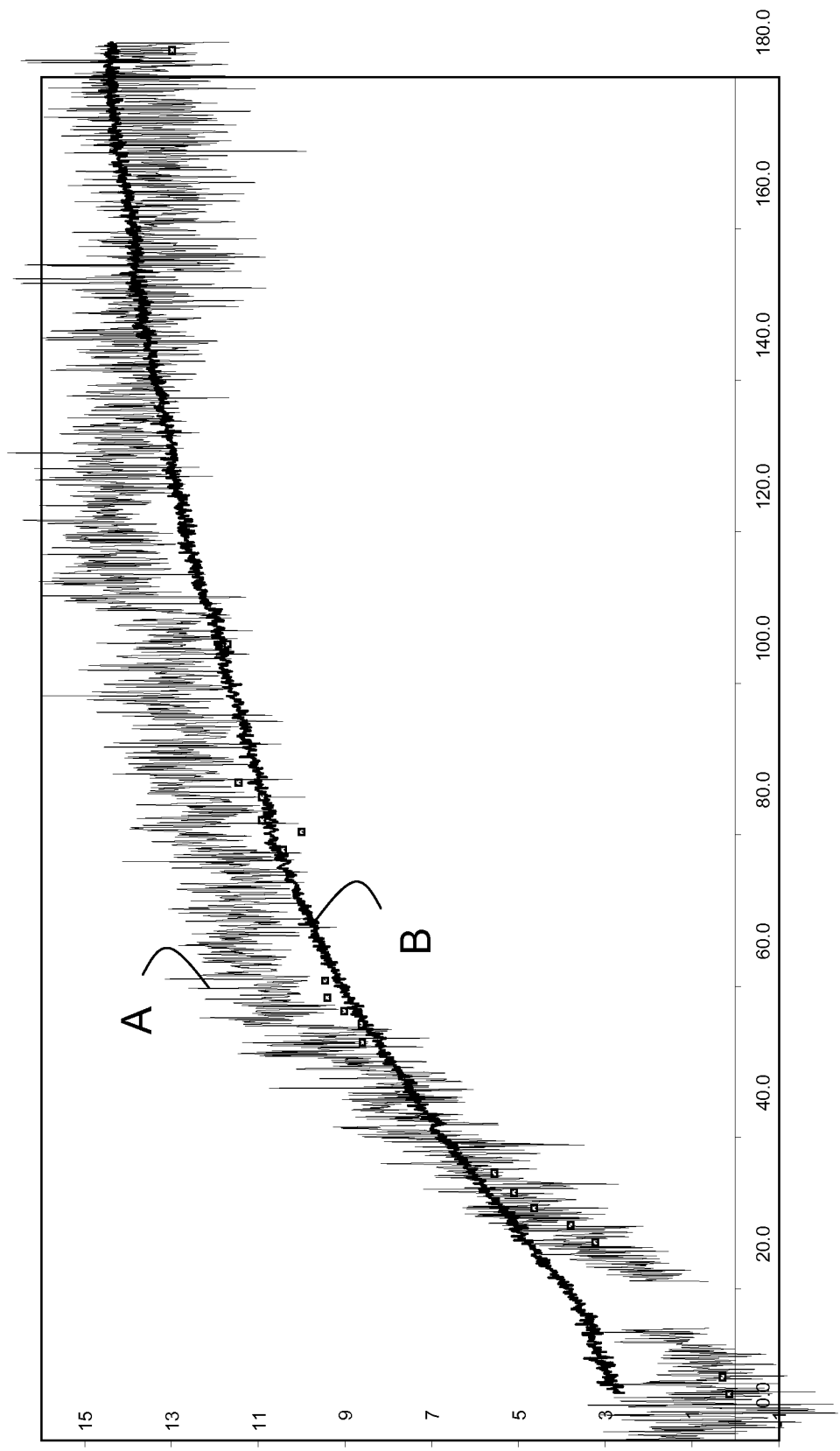
FIG. 18 shows raw and subtracted spectra, according to one embodiment.

Chemometric models were applied to the data using principal component analysis (PCA). FIG. 17 shows a fermentation plot with time (hours) on the x-axis and glucose concentration, A, (grams per liter) on the y-axis (left hand side scale) and ethanol concentration, B, (grams per liter) on the y-axis (right hand side scale). Data points represent HPLC data and show a good correlation for the mid-infrared spectral data shown as lines. FIG. 18 shows the benefits of using subtracted spectra data, B, (less noise) versus raw spectra data, A.

Figure 19:
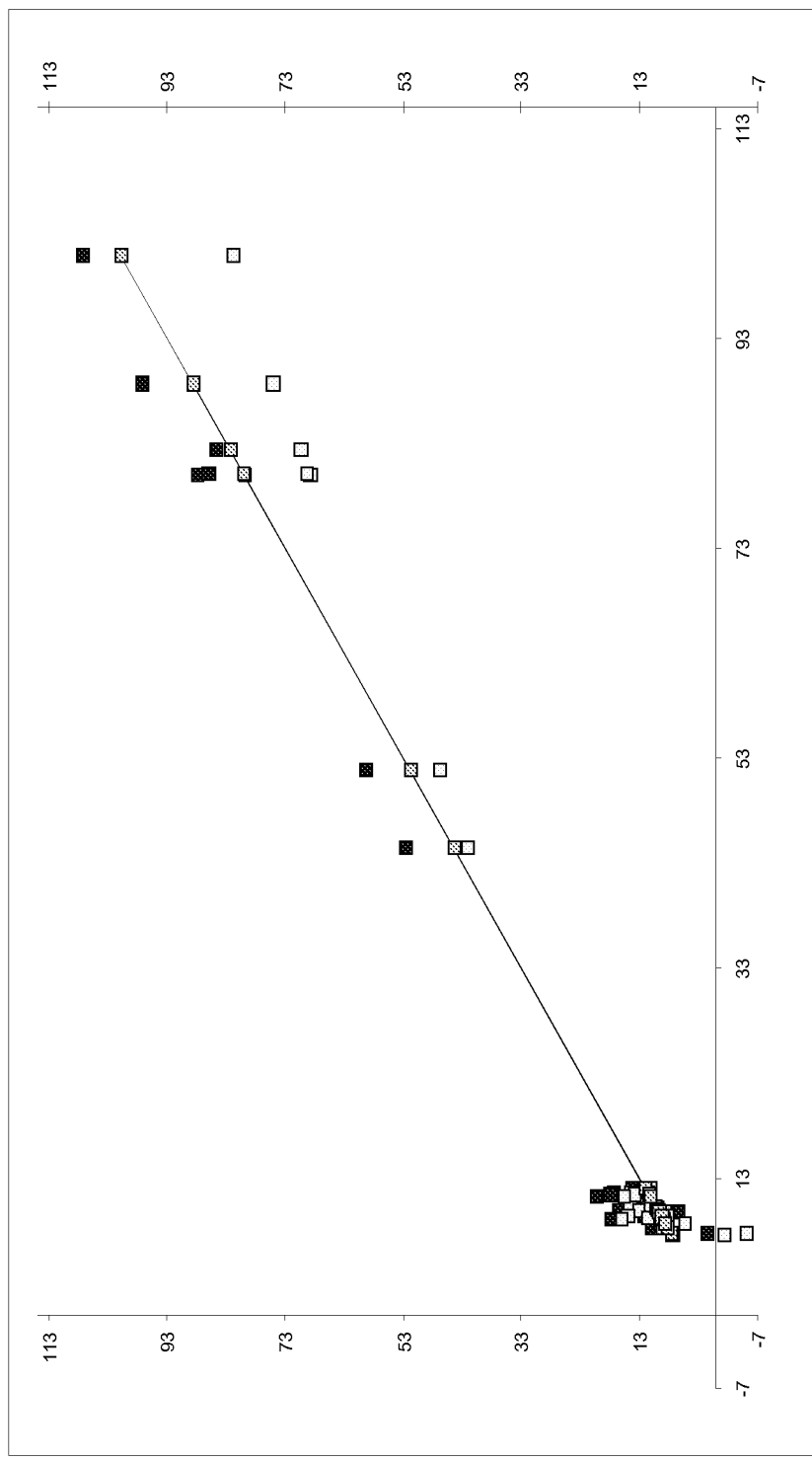
FIG. 19 shows a graph of component model accuracy, according to one embodiment.

FIG. 19 shows component model accuracy for glycerol with HPLC glycerol concentration on the x-axis (grams per liter) and predicted glycerol concentration (grams per liter) on the y-axis. The prediction had a root mean squared error of prediction for the subtracted spectra of 5.71 grams per liter. Model precision was explored by taking standard deviations of the predicted concentrations of the components during a period when the concentrations of the components were reasonably constant. The standard deviations ranged from 0.11 grams per liter to 0.85 grams per liter.

Figure 20:
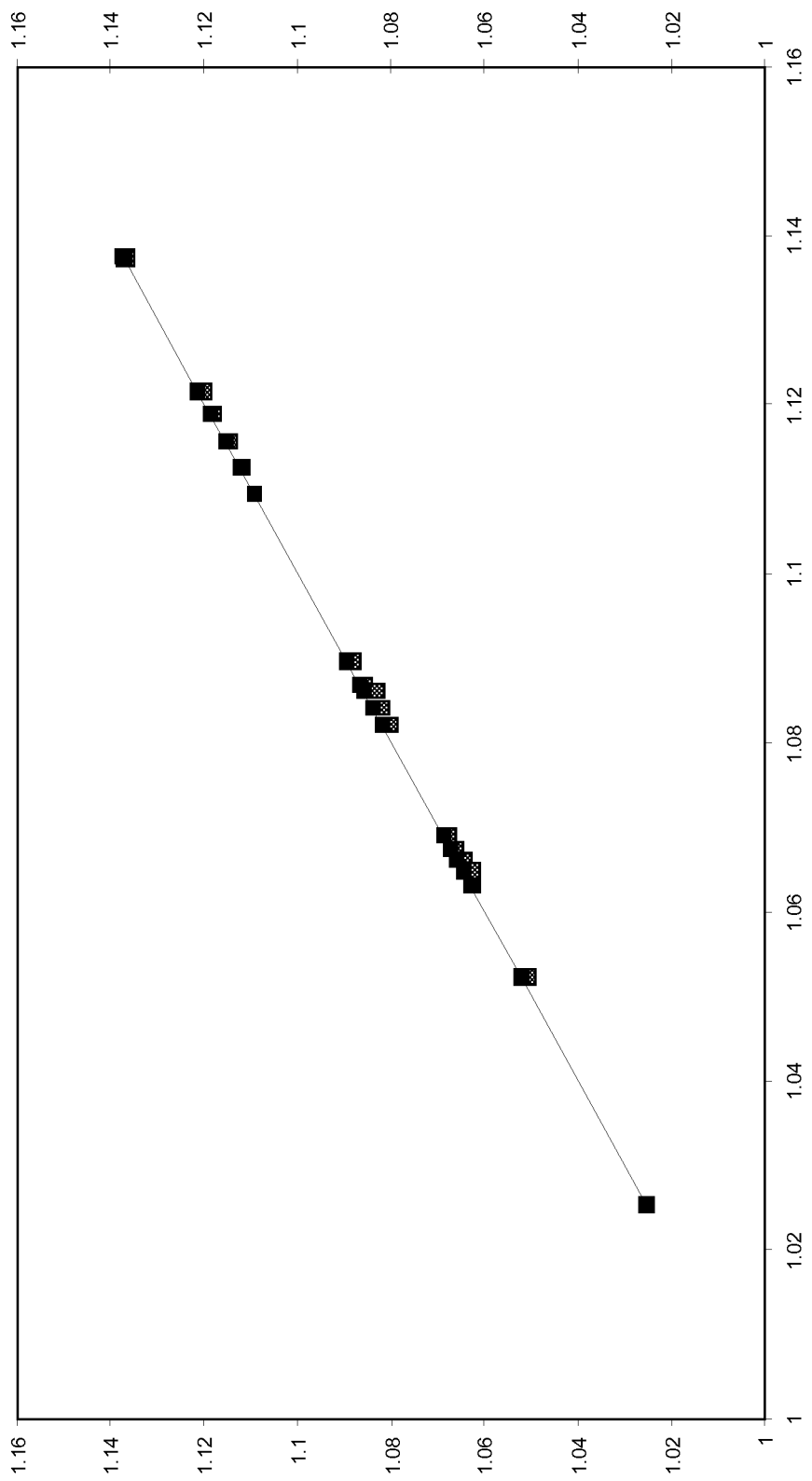
FIG. 20 shows a graph of gravity model accuracy, according to one embodiment.

A model was also developed to predict gravity or density of the fermentation mixture based on the mid-infrared spectra. 40 samples were used for gravity model calibration and 20 samples were used for validation. FIG. 20 shows a plot of measured gravity (grams per milliliter) on the x-axis and predicted gravity (grams per milliliter) on the y-axis. The root mean squared error prediction was only 0.0014 grams per liter.

The samples were tested again using a 3.4 bounce ATR probe which yielded similar results to those results of the 2 bounce probe discussed above.

A steam sterilization was conducted on the probe by raising water in the reactor to 121 degrees Celsius for 15 minutes before cooling to ambient temperature. Before sterilization the probe had a light throughput of 5,949 counts in water and 6,030 counts in water following sterilization. The probe was sterilized with no apparent loss of sensitivity. Sterilization of the probe was successful.

The invention has been described herein with respect to biological processes, however one of skill in the art may readily appreciate that the invention is not limited to such biological applications. Broader and varied applications and/or uses for the methods and apparatuses disclosed within this specification are within the scope of this invention.

As used herein the terms "having", "comprising", and "including" are open and inclusive expressions. Alternately, the term "consisting" is a closed and exclusive expression. Should any ambiguity exist in construing any term in the claims or the specification, the intent of the drafter is toward open and inclusive expressions.

As used herein the term "and/or the like" provides support for any and all individual and combinations of items and/or members in a list as well as support for equivalents of individual and combinations of items and/or members.

Regarding an order, number, sequence, and/or limit of repetition for steps in a method or process, the drafter intends no implied order, number, sequence and/or limit of repetition for the steps to the scope of the invention, unless explicitly provided.

Regarding ranges, ranges are to be construed as including all points between upper values and lower values, such as to provide support for all possible ranges contained between the upper values and the lower values including ranges with no upper bound and/or lower bound.

It will be apparent to those skilled in the art that various modifications and variations can be made in the disclosed structures and methods without departing from the scope or spirit of the invention. Particularly, descriptions of any one embodiment can be freely combined with descriptions of other embodiments to result in combinations and/or variations of two or more elements and/or limitations. Other embodiments of the invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. A method of measuring biological processes, the method comprising:
    directing a mid-infrared signal into an initial sample of a biological process before a biologically active phase;
    detecting a sample spectrum from the mid-infrared signal to form an initial sample spectrum before the biologically active phase;
    generating an initial reference spectrum through a reference media comprising water, fermentation material, fiber optic cable, or combinations thereof, before the biologically active phase;
    combining the initial sample spectrum and the initial reference spectrum to form an adjusted initial sample spectrum;
    subtracting the adjusted initial sample spectrum from the adjusted sample spectrum to form a difference spectrum;
    directing a the mid-infrared signal into a sample of a the biological process during the biologically active phase;
    detecting a sample spectrum from the mid-infrared signal to form a sample spectrum;
    generating a reference spectrum through a the reference media; and
    combining the sample spectrum and the reference spectrum to form an adjusted sample spectrum.

2. The method of claim 1 wherein the mid-infrared signal comprises wave numbers of between about 4,000 centimeters$^{-1}$ to about 400 centimeters$^{-1}$.

3. The method of claim 1, wherein the mid-infrared signal penetrates into the sample between about 1 micron and about 10 microns.

4. The method of claim 1, wherein the sample spectrum contains values corresponding to molecular stretching, molecular bending, or combinations thereof.

5. The method of claim 1, wherein the sample spectrum contains values corresponding to carbon-oxygen bonds, carbon-nitrogen bonds, or combinations thereof.

6. The method of claim 1, wherein the directing a mid-infrared signal utilizes attenuated total reflectance having at least 1 reflection of the mid-infrared signal off an internal surface in fluid communication with the at least a portion of the biological process.

7. The method of claim 1, wherein the sample spectrum contains values corresponding to acetone, acetaldehyde, ethanol, butanol, pentanol, isoprenol, isoprene, butyraldehyde, acetic acid, lactic acid, pyruvic acid, glycerol, pentose, hexose, fatty alcohols, fatty acids, acylgylcerides, carbon dioxide, carbon monoxide, or combinations thereof.

8. The method of claim 1, wherein the biological process comprises production of renewable materials.

9. The method of claim 1, wherein the biological process comprises biomass fermentation to an alcohol.

10. The method of claim 1, wherein the detecting a sample spectrum from the mid-infrared signal to form a sample spectrum comprises detecting the mid-infrared signal reflected or transmitted from the sample of the biological process.

11. The method of claim 1, further comprising:
    displaying one or more spectra on a display screen;
    printing one or more spectra on a printing substrate; or
    recording one or more spectra on a recording media.

12. A method of measuring biological processes, the method comprising:
    directing a mid-infrared signal into an initial sample of a biological process, wherein. the mid-infrared signal comprises wave numbers of between about 4,000 centimeters$^{-1}$ to about 400 centimeters$^{-1}$;
    detecting a sample spectrum from the mid-infrared signal to form an initial sample spectrum;
    generating an initial reference spectrum through a reference media comprising fiber ,optic cable;
    combining the initial sample spectrum and the initial reference spectrum to form an adjusted initial sample spectrum;
    directing the mid-infrared signal into one or more subsequent samples of the biological process;
    detecting a sample spectrum from the mid-infrared signal to form one or more subsequent sample spectra;
    generating one or more subsequent reference spectra through the reference media corresponding to each of the one or more subsequent sample spectra;
    combining the one or more subsequent sample spectra and the corresponding one or more subsequent reference spectra to form one or more adjusted subsequent sample spectra; and
    subtracting the adjusted initial sample spectrum from each of the one or more adjusted subsequent sample spectra to form one or more difference spectra.

13. The method of claim 12, wherein the biological process comprises batch biomass fermentation to an alcohol.

14. The method of claim 12, further comprising combining the one or more difference spectra to generate one or more time dependent spectra.

* * * * *